(12) United States Patent
Gautam et al.

(10) Patent No.: US 8,580,517 B2
(45) Date of Patent: Nov. 12, 2013

(54) BIOSENSOR AND USE THEREOF TO IDENTIFY THERAPEUTIC DRUG MOLECULES AND MOLECULES BINDING ORPHAN RECEPTORS

(75) Inventors: Narasimhan Gautam, St. Louis, MO (US); Inaki Azpiazu, St. Louis, MO (US)

(73) Assignee: Washington University in St. Louis, St. Louis, MO (US)

( * ) Notice: Subject to any disclaimer, the term of this patent is extended or adjusted under 35 U.S.C. 154(b) by 1711 days.

(21) Appl. No.: 10/771,897

(22) Filed: Feb. 4, 2004

(65) Prior Publication Data
US 2004/0224361 A1 Nov. 11, 2004

Related U.S. Application Data

(60) Provisional application No. 60/445,113, filed on Feb. 5, 2003, provisional application No. 60/493,952, filed on Aug. 8, 2003.

(51) Int. Cl.
*G01N 33/53* (2006.01)
*C12N 5/07* (2010.01)

(52) U.S. Cl.
USPC .......... 435/7.1; 435/287.1; 435/325; 500/350

(58) Field of Classification Search
USPC .................. 530/350; 435/325, 7.1, 287.1
See application file for complete search history.

(56) References Cited

U.S. PATENT DOCUMENTS

| 2002/0048811 A1* | 4/2002 | Devreotes et al. | 435/325 |
| 2002/0182655 A1* | 12/2002 | Kostenis et al. | 435/7.21 |
| 2003/0104478 A1* | 6/2003 | Wittamer et al. | 435/7.1 |

OTHER PUBLICATIONS

Ruiz-Velasco, V. et al., "Functional expression and FRET analysis of green fluorescent protein fused to G-protein subunits in rat sympathetic neurons," J. Physiol. 537: 679-692 (Dec. 15, 2001).
USPTO Office Action dated May 14, 2010 for U.S. Appl. No. 10/914,049.

\* cited by examiner

*Primary Examiner* — Chih-Min Kam
(74) *Attorney, Agent, or Firm* — Armstrong Teasdale LLP

(57) ABSTRACT

G protein biosensors comprising mammalian G protein subunits fused to fluorescent proteins emitting a FRET signal expressed in living intact functional cells. The intensity of the FRET signal is strongly responsive to the activation state of the biosensors. The biosensors respond reproducibly to agonist and antagonist drug molecules specific for G protein coupled receptors. The biosensors have utility in identifying and classifying candidate therapeutic drugs as to their therapeutic value.

19 Claims, 31 Drawing Sheets

Activation/deactivation of G protein Biosensor in Biosensor Cell provides FRET Signal Response

Biosensor Cell responds to addition of Agonist Neurotransmitter Serotonin with decrease in FRET Signal Intensity Biosensor Cell responds to addition of Agonist Drug Adenosine N6-Cyclohexyl. with decrease in FRET Signal Intensity Biosensor Insect Cell responds to addition of Agonist Drug Carbachol with decrease in FRET Signal Intensity Fig. 17 Operation of G protein Biosensor Cell Fluorescence spectra from insect cells containing a biosensor made up of αo tethered to the receptor in the presence of an agonist and antagonist Fig. 27 Biosensor containing YFP tagged β and γ subunits

SEQUENCE LISTING

<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      DNA construct

<400> SEQUENCE: 1
ggtaccaaac tagt                                                    14

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaagtcgaac atgggatgta ctctgagcgc agaggagaga gccgcc                 46

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttagatctt cagtacaagc cacagccccg gagattgttg gc                     42

US 8,580,517 B2

BIOSENSOR AND USE THEREOF TO IDENTIFY THERAPEUTIC DRUG MOLECULES AND MOLECULES BINDING ORPHAN RECEPTORS

This application claims the individual and collective benefit of U.S. provisional patent application U.S. Ser. No. 60/445,113 filed Feb. 5, 2003 and U.S. provisional application U.S. Ser. No. 60/493,952 filed Aug. 8, 2003, both pending, each of which is incorporated herein in its respective entirety by reference.

STATEMENT REGARDING FEDERALLY SPONSORED RESEARCH AND DEVELOPMENT

This invention was made with government support under Grant Number GM46963 awarded by the National Institute of Health. The government has certain rights in the invention.

FIELD OF THE INVENTION

This invention relates to recombinant DNA technology and the preparation and operation of a functional biosensor capable of and capably operating in a living intact functional cell. More particularly, this invention relates to mammalian receptor stimulated G proteins and to a method of traditional or high content screening of candidate molecules non-invasively using a functional biosensor comprising G proteins in live intact functional cells to identify and classify candidate therapeutic drug molecules and to identify potential therapeutic efficacy.

BACKGROUND OF THE INVENTION

G proteins and their receptors play a key controlling and decisive role in regulating cellular physiology [1]. Some of the regulatory signaling pathways mediated by receptors and G proteins are implicated in the onset and progression of serious and fatal human diseases. G proteins comprise an α subunit and a βγ subunit complex. G proteins are signal transducers—that is they mediate the conversion of an extracellular signal into an intracellular physiological response. On sensing a hormone, neurotransmitter, a natural or chemically synthesized agonist, an excited receptor activates a G protein resulting in the dissociation of the α subunit and βγ complex which subsequently regulate the function of effectors inside the cell. (See also BIOCHEMISTRY, Third Edition, Lubert Stryer, W.H. Freeman and Company, N.Y., in particular Chapter 38 thereof, including page 979).

In live mammalian systems such as human, rat and mice, G protein signaling pathways are extraordinarily complex compared to G protein signaling pathways in single cell organisms such as yeast (*Saccharomyces cerevisiae*) and soil amoeba (*Dictyostelium discoideum*). Yeast and soil amoeba cells contain a few G protein coupled receptor types and G protein types while in contrast mammalian cells contain hundreds of G protein coupled receptor types and a large variety of G protein subunit types [2].

Many of the molecular mechanisms underlying G protein signaling pathways have so far been elucidated in in vitro systems using purified proteins and broken cells. However, G protein signaling operations occur in intact living cells subject to constraints of dynamic equilibrium, which are disrupted when cells are broken.

Additionally, as mentioned before, mammalian cells contain large families of G protein subunits, receptors and effector molecules leading to the generation of vast networks of membrane transduction signaling pathways which are functional only when the cell is intact and living [3]. Unfortunately, relatively little information is at present available about the behavior of these signaling pathways in an intact living mammalian cell because methods have not been available for their observation.

Several mechanisms at the basis of G protein signaling have been identified so far. Results have shown that receptor stimulated dissociation of the G protein subunits leads to the activation of effectors downstream and thus signaling pathways. Both activated subunits, the GTP bound α subunit and the βγ complex, act on effector molecules [4]. Subsequent formation of the G protein heterotrimer as a result of receptor inactivation, switches off effector signaling activity of the G protein subunits. In order to elucidate more information, soil amoeba (*D. discoideum*) G protein subunits have been labeled with fluorescent proteins and expressed in soil amoeba (*D. discoideum*) cells providing the capability of detecting a FRET signal emanating from a heterotrimer and detecting the loss of FRET signal upon activation and subsequent dissociation of the heterotrimer [5].

G protein coupled receptors form the single largest target for commercially available pharmaceutical drugs today. It is estimated that fifty percent of recently launched drugs were targeted at these receptors with annual worldwide sales exceeding about $30 billion in year 2001. Among the one hundred highest selling drugs, about 25% were directed at G protein coupled receptors [6].

However, today's available commercial drugs are targeted at a relatively small proportion of known G protein coupled receptors.

While the three dimensional structure of the G protein coupled receptor and newer methods of rational drug design increase the range and depth of candidate molecules are available, there is at present an undesired serious limitation in methods available to screen drug candidates non-invasively using mammalian G protein coupled receptors and G proteins.

There is also a lack of information about the temporal changes and spatial localization of the effects of candidate therapeutic molecules in an intact living cell.

BRIEF DESCRIPTION OF THE INVENTION

In a first aspect, a mammalian functional biosensor comprises a mammalian G protein signaling subunit(s) fused to cyan fluorescent protein and yellow fluorescent protein respectively and capably enabled for fluorescence resonance energy transfer.

In another aspect, a live functional G protein biosensor comprises a mammalian α subunit comprising a first amino acid sequence encoding a first fluorescent or a luminescent protein and a mammalian βγ subunit complex comprising a second amino acid sequence encoding a second different fluorescent or a luminescent protein, wherein said first and said second fluorescent or luminescent proteins are at least FRET or BRET capable.

In an aspect, a live functional G protein biosensor cell comprises a mammalian α subunit comprising at least one first amino acid sequence encoding a first fluorescent or luminescent protein fused (tethered) to a mammalian G protein coupled receptor C terminus and a mammalian βγ subunit complex comprising a second amino acid sequence encoding a second fluorescent or a luminescent protein, wherein said first and said second fluorescent or luminescent proteins are at least FRET or BRET capable. In an aspect, the second fluorescent or luminescent protein are different from the first fluorescent or luminescent protein.

In an aspect, a screening method for screening natural or chemically synthesized candidate agonists and antagonists that bind to previously characterized, uncharacterized or "orphan" mammalian receptors comprises operating an intact living cell containing said receptors and fluorescent protein tagged mammalian G protein α subunits and βγ subunit complexes that are FRET capable to a candidate agonist or a candidate antagonist which when exposed to said candidate agonists elicit a decrease in FRET signal and which when exposed to an antagonist results in an increase in the FRET signal thereby identifying respective agonist(s) and antagonist(s) for characterized, uncharacterized or orphan receptor. In an aspect, exposure to an antagonist follows exposure to an agonist.

In an aspect, a non-invasive method for identifying a candidate therapeutic drug molecule comprises obtaining a FRET output as a profile over a time period from a live functional biosensor cell comprising a mammalian α subunit comprising a first amino acid sequence encoding a first fluorescent protein and a mammalian betagamma subunit complex comprising a second amino acid sequence encoding a second fluorescent protein, wherein said first and said second fluorescent or luminescent proteins are fluorescence resonance energy transfer capable and are expressed in cells containing a receptor or an orphan receptor (a) in the absence of an added candidate molecule, (b) in the presence of an added molecule and then comparing a FRET profile of (b) with a FRET profile of (a) to obtain a comparison of the FRET profile of (b) with the FRET profile of (a).

A live functional G protein biosensor cell comprising a mammalian alpha subunit comprising a first amino acid sequence encoding a first fluorescent or luminescent protein, and a beta subunit comprising a second amino acid sequence encoding a second fluorescent or luminescent protein, wherein said first amino acid sequence is fused to said second mammalian beta subunit comprising a second amino acid sequence encoding a second fluorescence or luminescent protein.

A method of classifying candidate therapeutic molecules as agonists, antagonists or inverse agonists using biosensor cells encoding and expressing the fluorescent protein tagged alpha subunit fused to a second fluorescent protein tagged beta subunit with a gamma subunit and screening for predicted changes in the FRET profile from these cells in response to the addition of the candidate molecules.

A method for identifying and classifying candidate therapeutic molecules which are agonists, antagonists or inverse agonists of various receptor types by performing high content screening of biosensor cells wherein 'high content' is defined as information about biosensor activity in terms of both time dependence and spatial location in an intact cell maintaining structural and functional integrity. A method for identifying and classifying candidate therapeutic molecules which are agonists, antagonists or inverse agonists of various receptor types by performing high content screening of biosensor cells wherein 'high content' is defined as information about biosensor activity in terms of both time dependence and spatial location in an intact cell maintaining structural and functional integrity.

Figure 4:
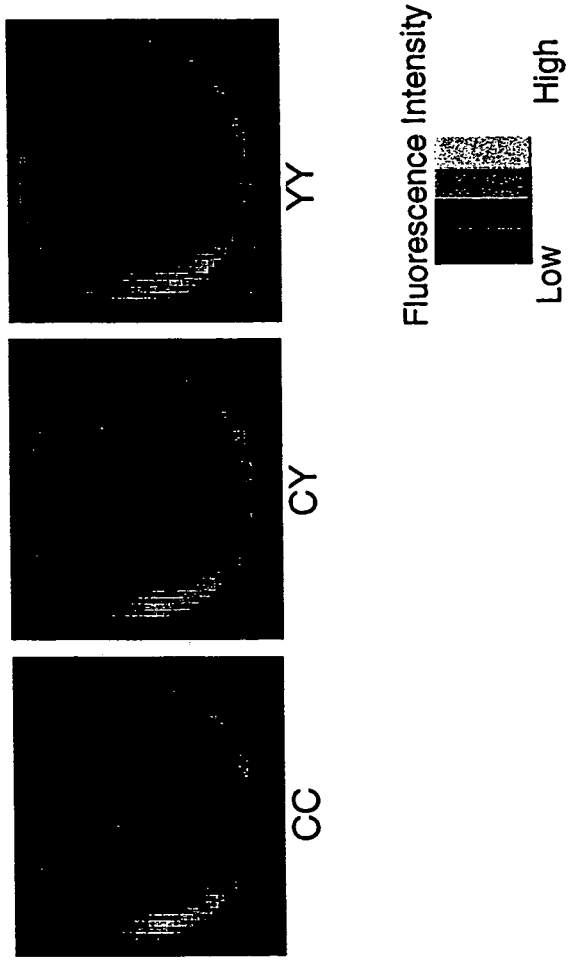
In FIG. 4, parts CC, CY and YY show measured emitted fluorescence (Spectra) from Chinese Hamster Ovary (CHO) cells stably expressing a G protein biosensor and M2 muscarinic acetylcholine receptors. These functional biosensor cells were imaged as described in the Detailed Description of the Invention.

More in detail, FIG. 4 CC shows a functional biosensor cell excited using a 436/20 nm excitation filter and emission acquired using a 480/40 nm emission filter (denoted CC).

More in detail, FIG. 4 CY shows the same biosensor cell was excited using a 436/20 nm filter and emission acquired using a 535/30 nm filter.

More in detail, FIG. 4 YY shows the same biosensor cell excited using a 500/20 nm filter and emission acquired using a 535/30 nm. Images have been processed using MetaVue and/or Metamorph software. Brightness in pixels is positively correlated with expression level (i.e., fluorescence) of the fluorescent protein tagged protein.

Figure 5:
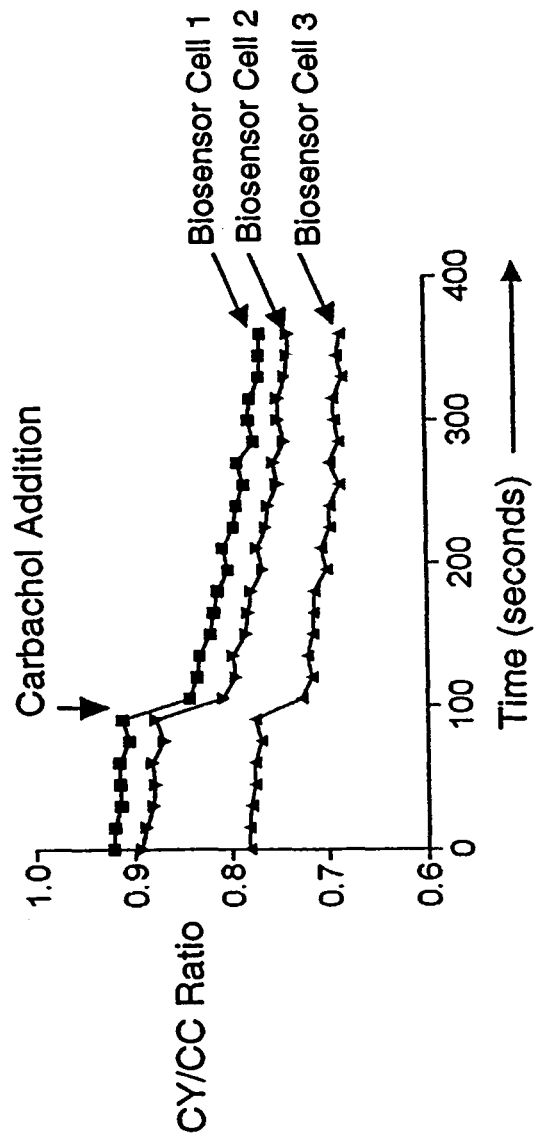

FIG. 5 is a graph of FRET profile (CY/CC) from three different functional biosensor cells (□∇Δ) before and after exposure to agonist drug molecule carbachol (1 mM).

Figure 6:
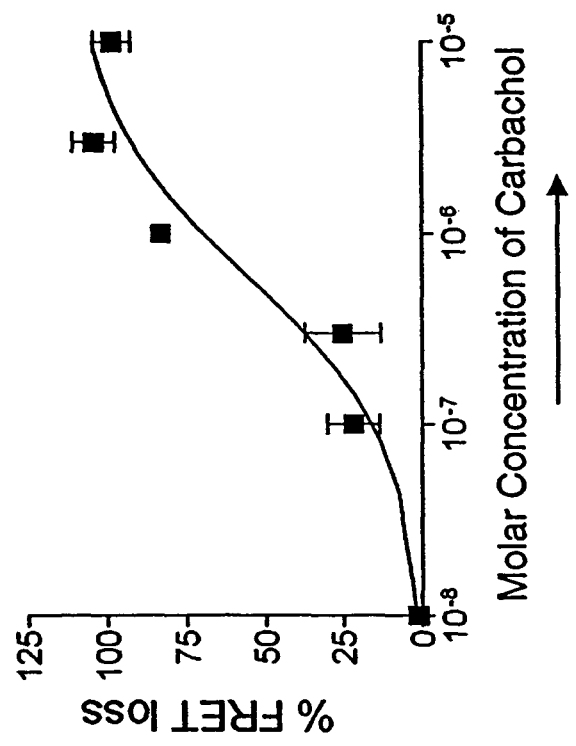

FIG. 6 is a graph of FRET profile (CY/CC) showing the magnitude of decrease in FRET signal intensity in functional biosensor cells in response to various concentrations of agonist drug carbachol.

Figure 7:
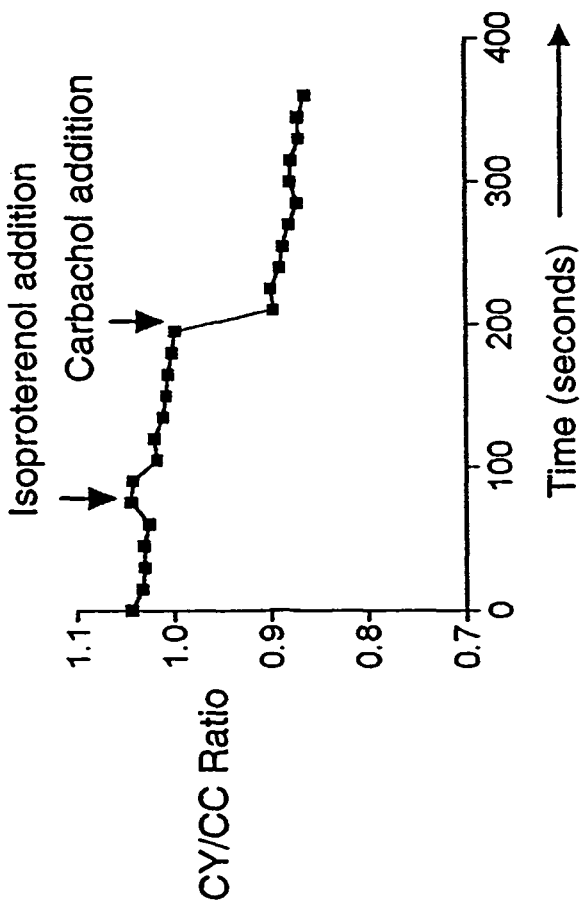

FIG. 7 is a graph of FRET profile (CY/CC) of a functional biosensor cell when a molecule specific for β adrenergic receptors was added that does not bind to the muscarinic acetylcholine receptor.

Figure 8:
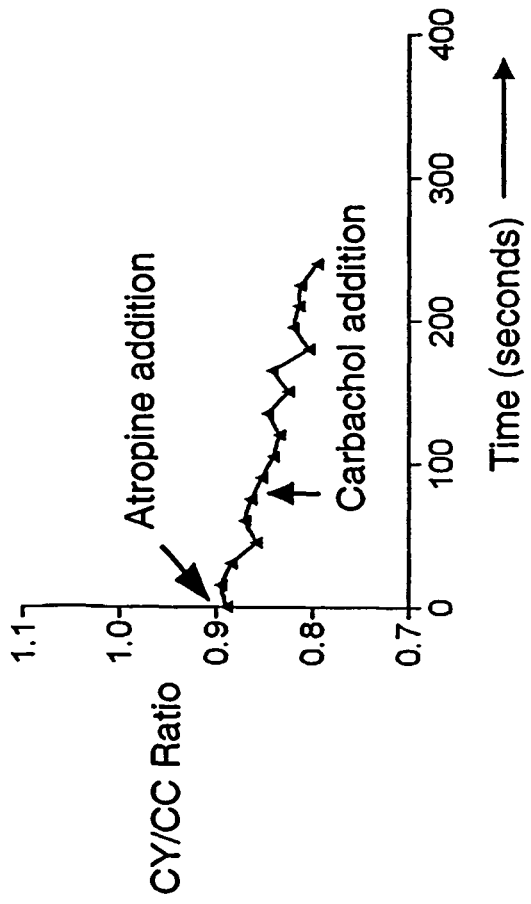

FIG. 8 shows a graph of FRET profile (CY/CC) from expressed functional biosensor cells of the effect of addition of carbachol (100 μM), on FRET signal intensity when added in the presence of a muscarinic acetylcholine receptor specific antagonist drug, atropine (10 μM) (Δ).

Figure 9:
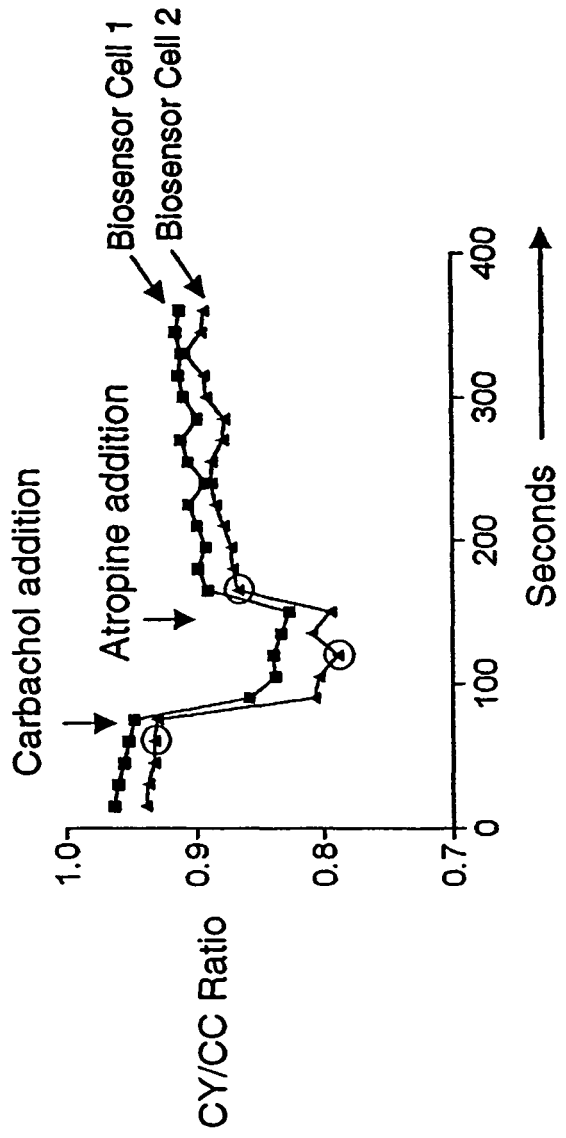

FIG. 9 shows a graph of a FRET profile (CY/CC) that shows decrease in FRET signal intensity from biosensor cells induced by an agonist drug, carbachol (100 μM) and the increase in FRET signal intensity induced by the subsequent addition of an antagonist drug, atropine (100 μM) to two different biosensor cells.

Figure 10:
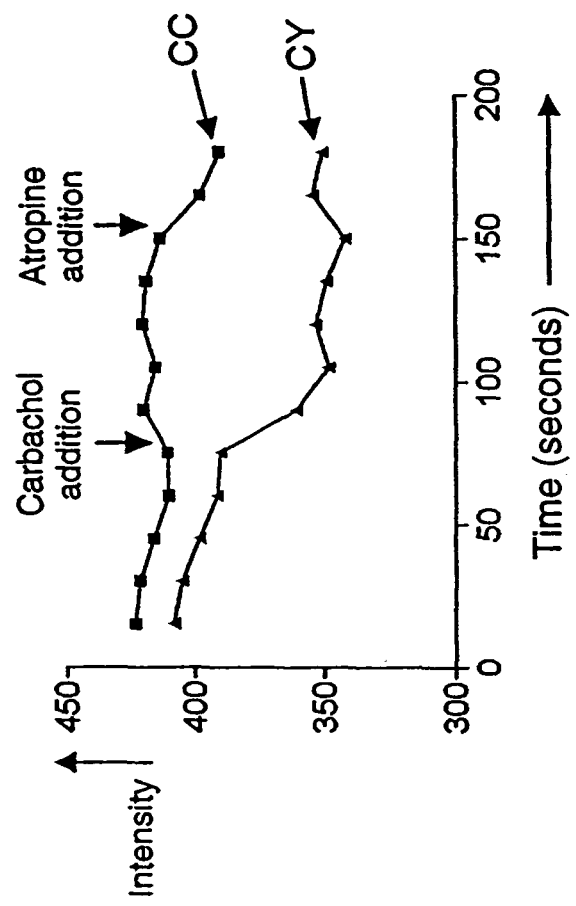

FIG. 10 shows a graph of FRET profile CC and FRET profile CY corresponding to one of the CY/CC FRET profiles above (□).

Figure 11:
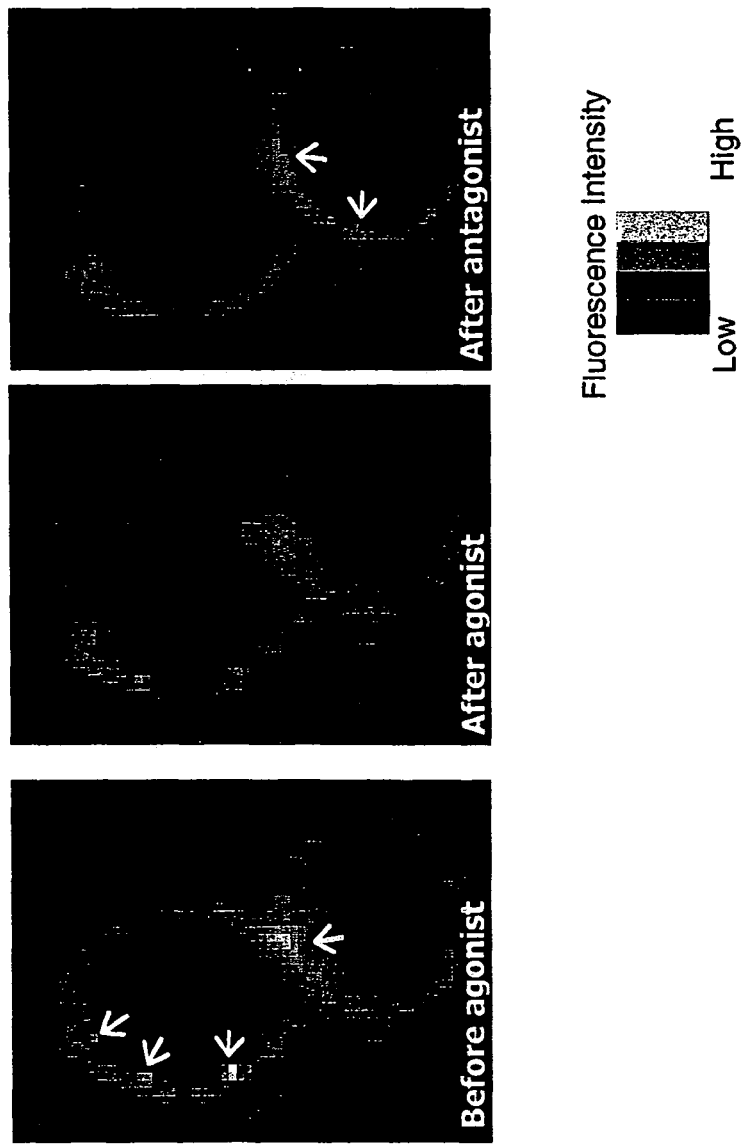

FIG. 11 shows a graph of CY images captured at time points before and after agonist or antagonist drugs were added to the biosensor cell. Images correspond to points noted in FIG. 9.

Figure 12:
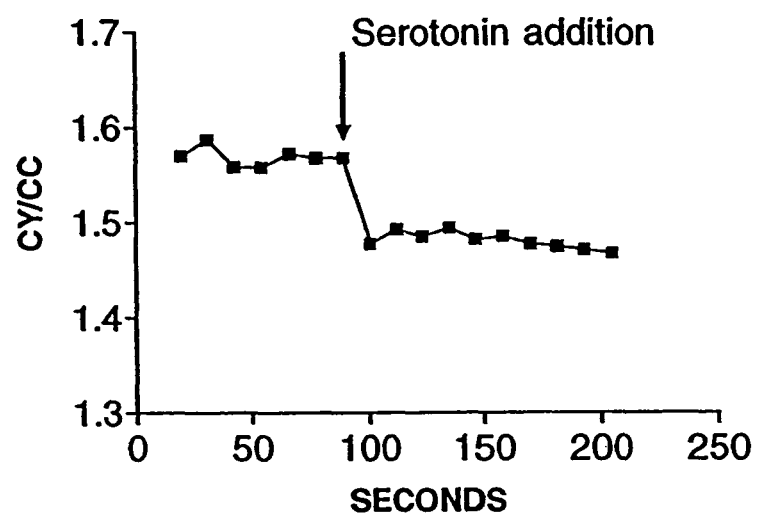

FIG. 12 is a graph of FRET profile showing the decrease in FRET signal intensity induced by the addition of an agonist neurotransmitter molecule, serotonin (20 μM) to biosensor cells expressing human serotonin receptors (Type 1A) instead of muscarinic acetylcholine receptors.

Figure 13:
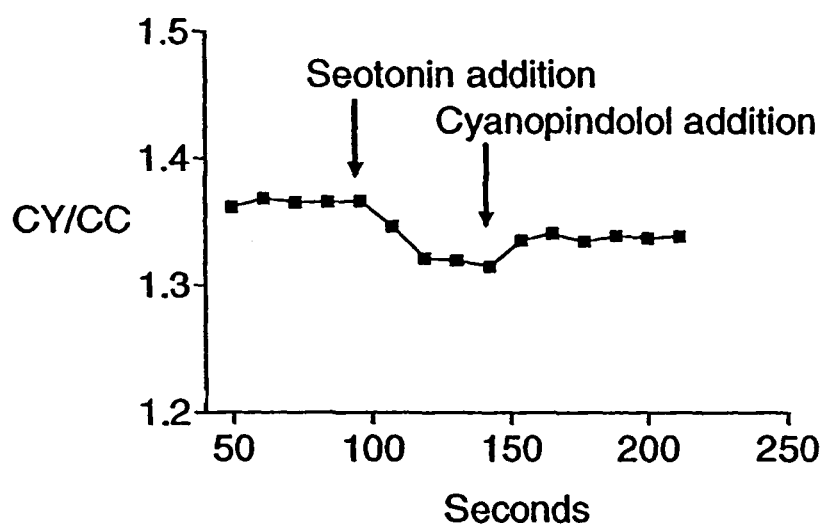

FIG. 13 is a graph of FRET profile showing the decrease in FRET signal intensity induced by the addition of serotonin (20 μM) to biosensor cells expressing serotonin receptors 2 and the increase in FRET signal intensity resulting from the subsequent addition of an antagonist drug specific to these receptors, cyanopindolol (150 μM).

Figure 14:
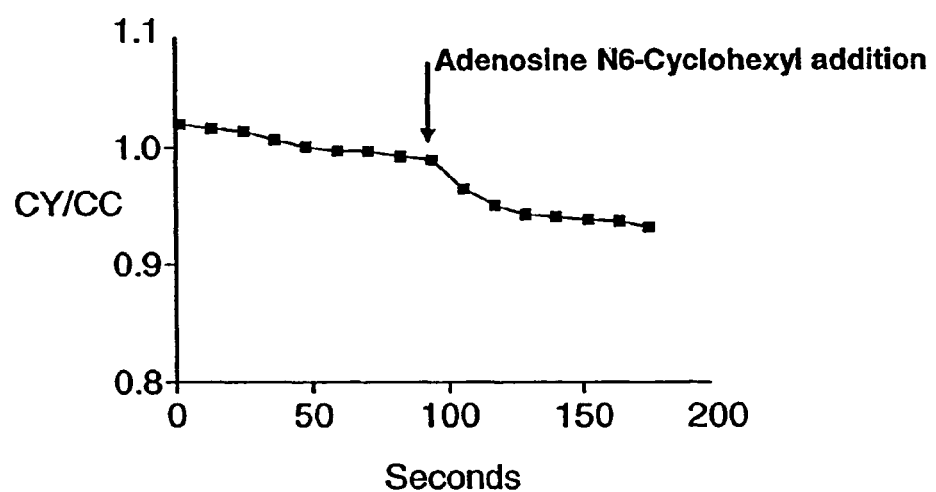

FIG. 14 is a graph of FRET profile showing the decrease in FRET signal intensity induced by the addition of an agonist drug adenosine N6-Cyclohexyl (50 μM) to biosensor cells expressing human adenosine receptors instead of muscarinic acetylcholine receptors.

Figure 15:
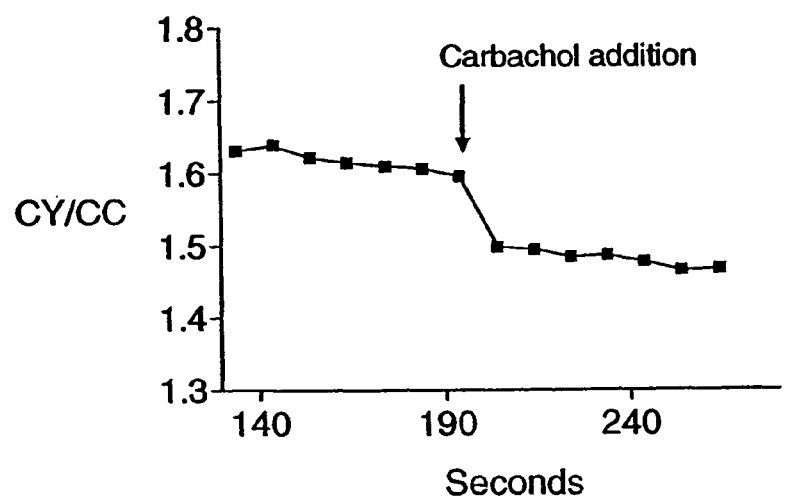

FIG. 15 is a graph of FRET profile showing a decrease in FRET signal intensity induced by the addition of carbachol to insect cells (Sf9) expressing the G protein biosensor and the M2 muscarinic acetylcholine receptor. Biosensor and receptor were expressed using the baculovirus system.

Figure 16:
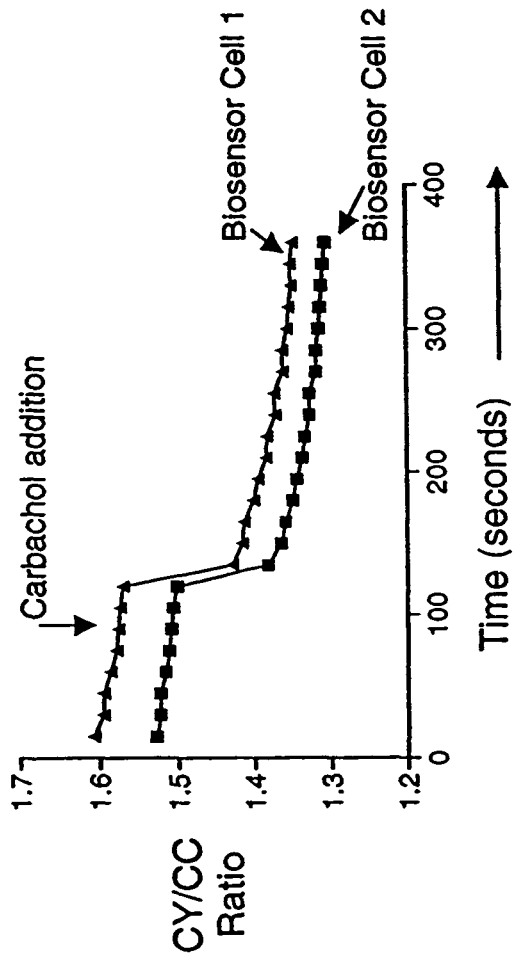

FIG. 16 shows a graph of FRET profiles from two different biosensor cells containing CFP tagged α subunit and YFP tagged γ subunit and untagged β subunit in CHO cells stably expressing M2 muscarinic receptors. This biosensor demonstrates properties similar to the biosensor α-CFP, β-YFPγ biosensor responding strongly to the addition of carbachol with a decrease in FRET signal intensity.

Figure 17:
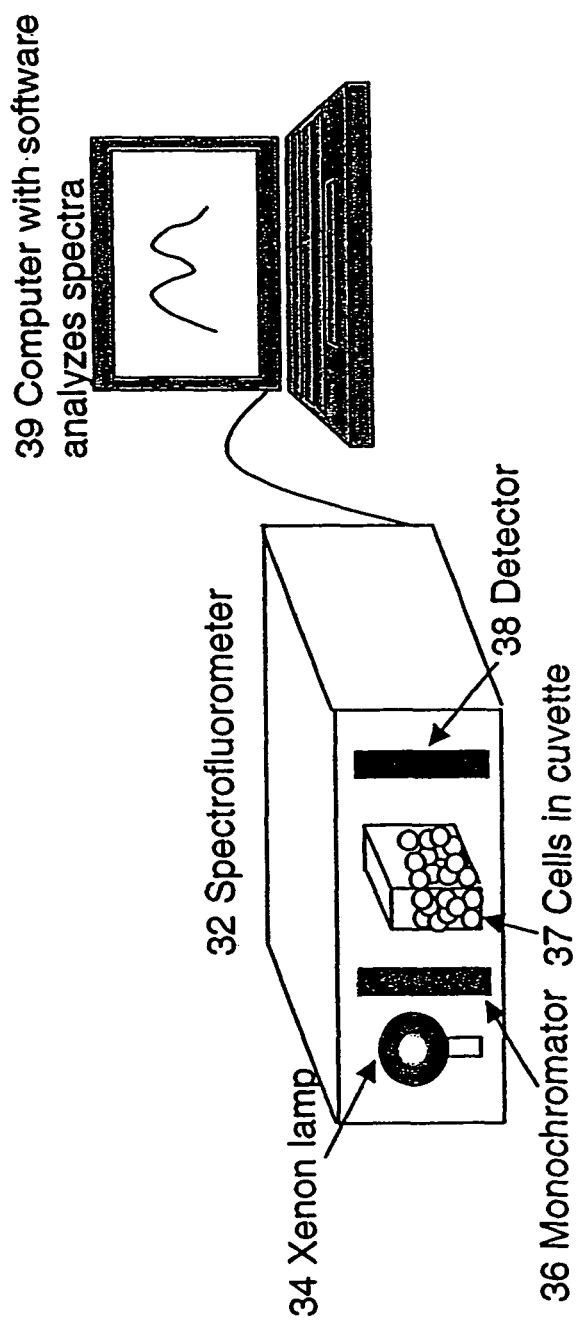

FIG. 17 provides a graph of an illustrative flow diagram of a biosensor cell operation using a spectrofluorometer.

Figure 18:
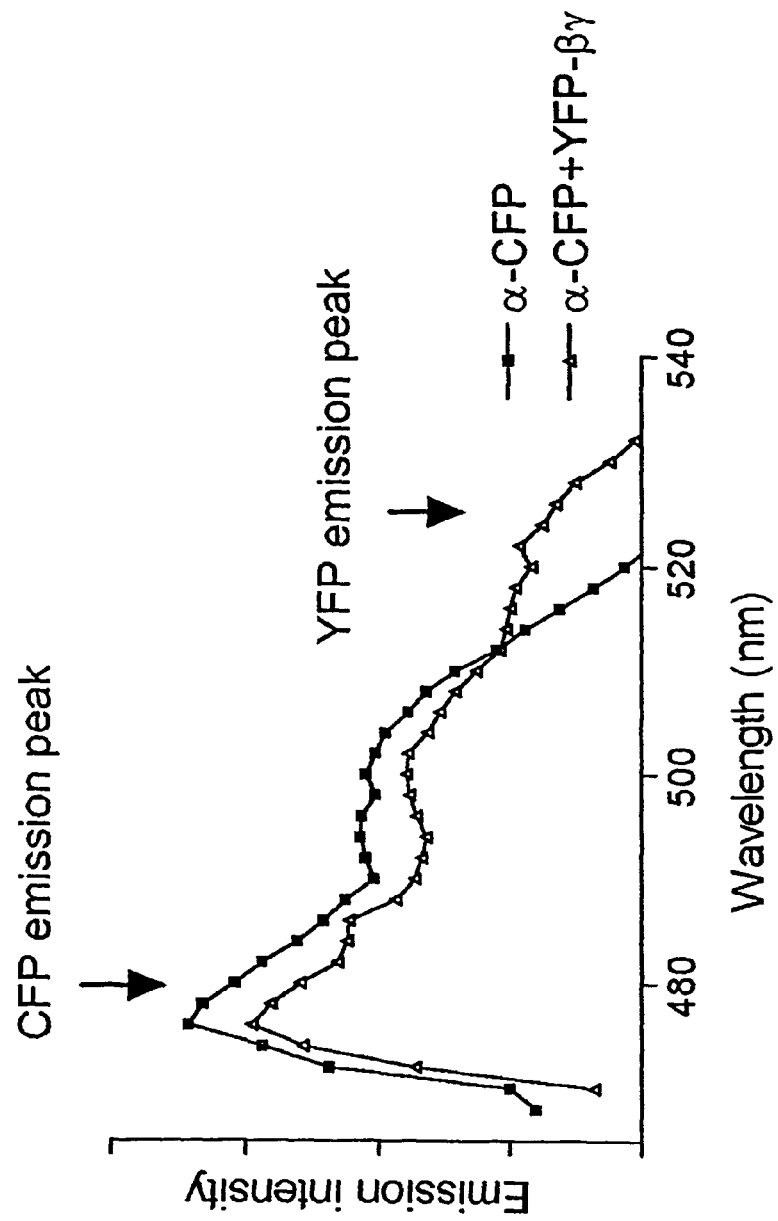

FIG. 18 depicts a graph of spectra from cells expressing biosensor or individual components of the biosensor.

Figure 19:
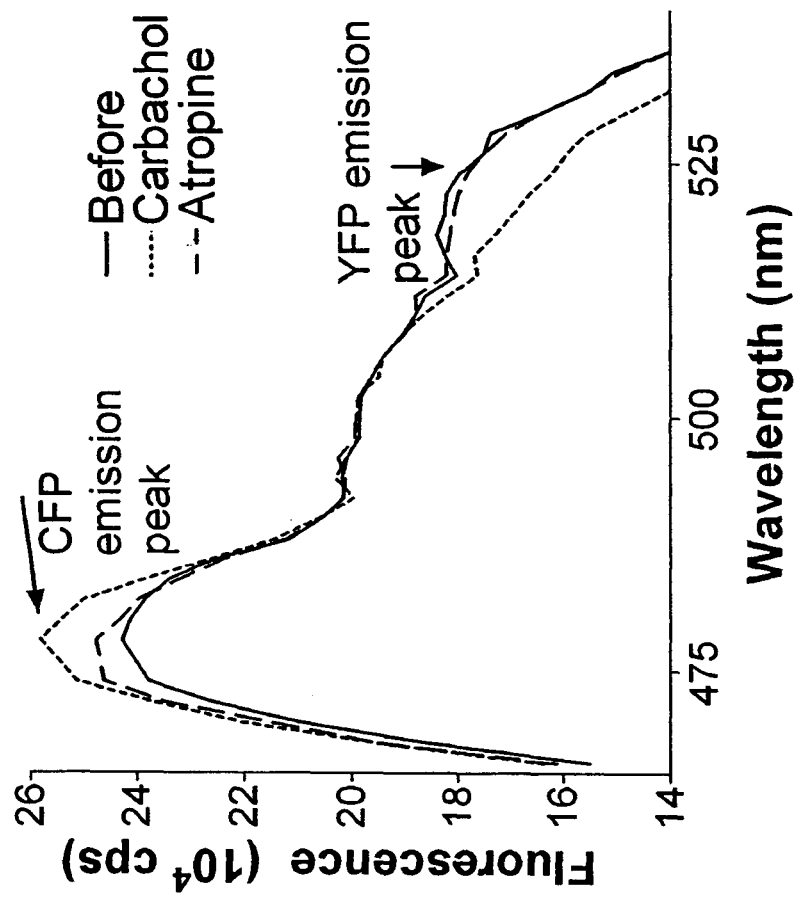

FIG. 19 depicts a graph of spectra from biosensor cells captured before activation with the agonist, after addition of agonist and then subsequent addition of the antagonist.

Figure 20:
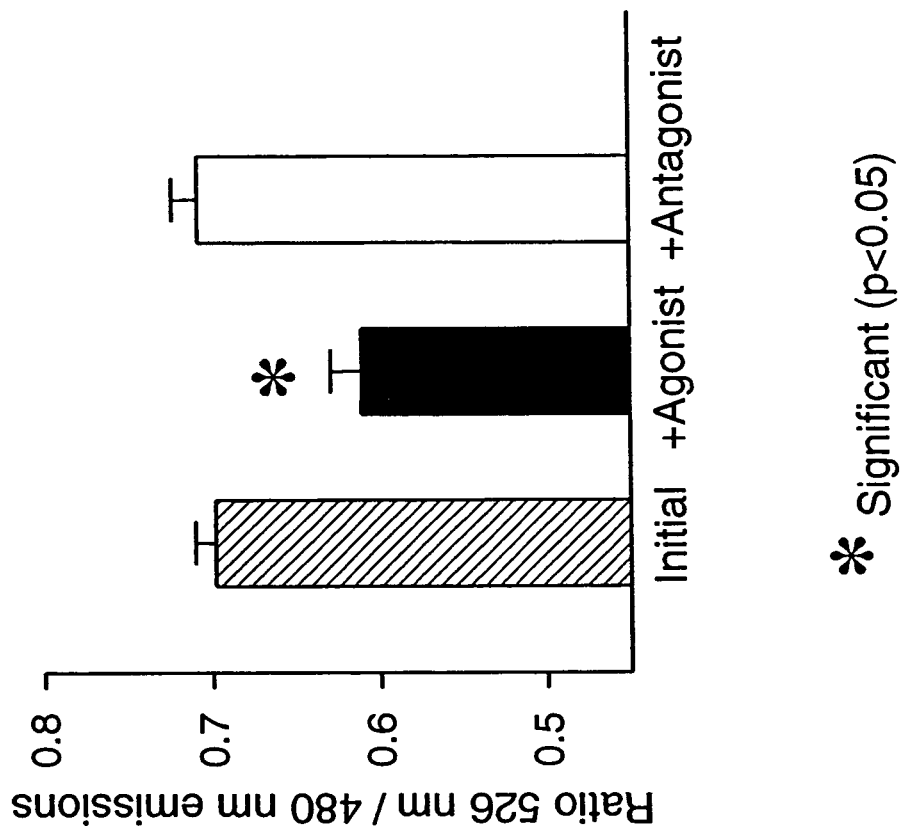

FIG. 20 depicts a graph of the mean ratios of emission at 526 nm (YFP emission peak) and 480 nm (CFP emission peak) from the different spectra from spectra similar to those in FIG. 19 above.

Figure 21:
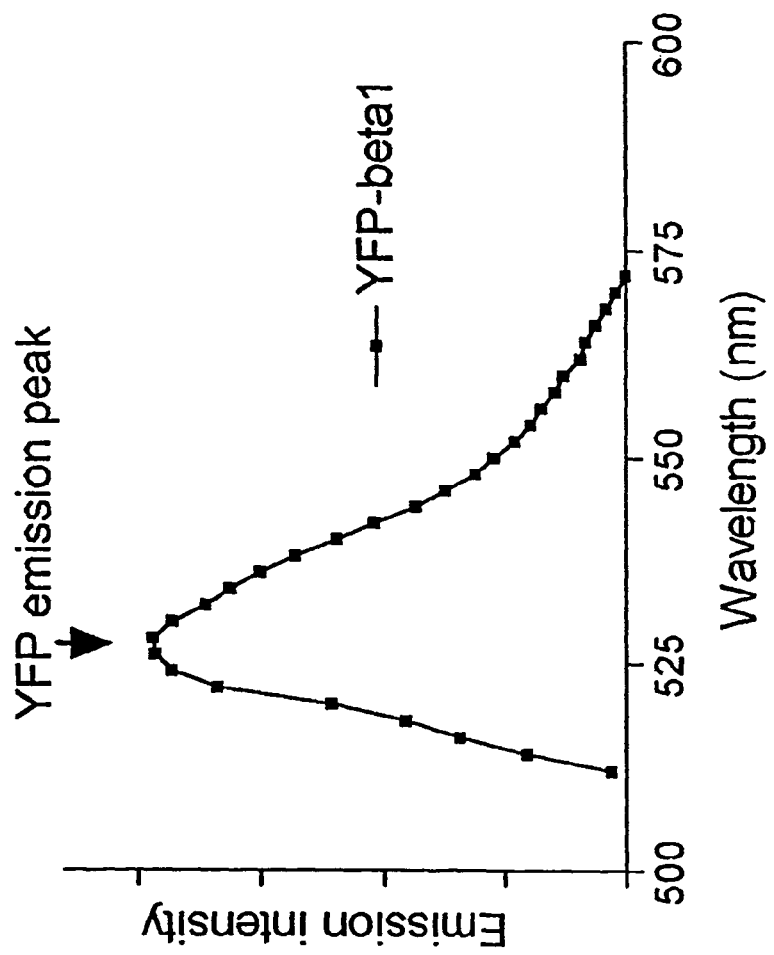

FIG. 21 depicts a graph of spectrum from biosensor cells excited at 485 nm to demonstrate presence of YFP in the cells.

Figure 22:
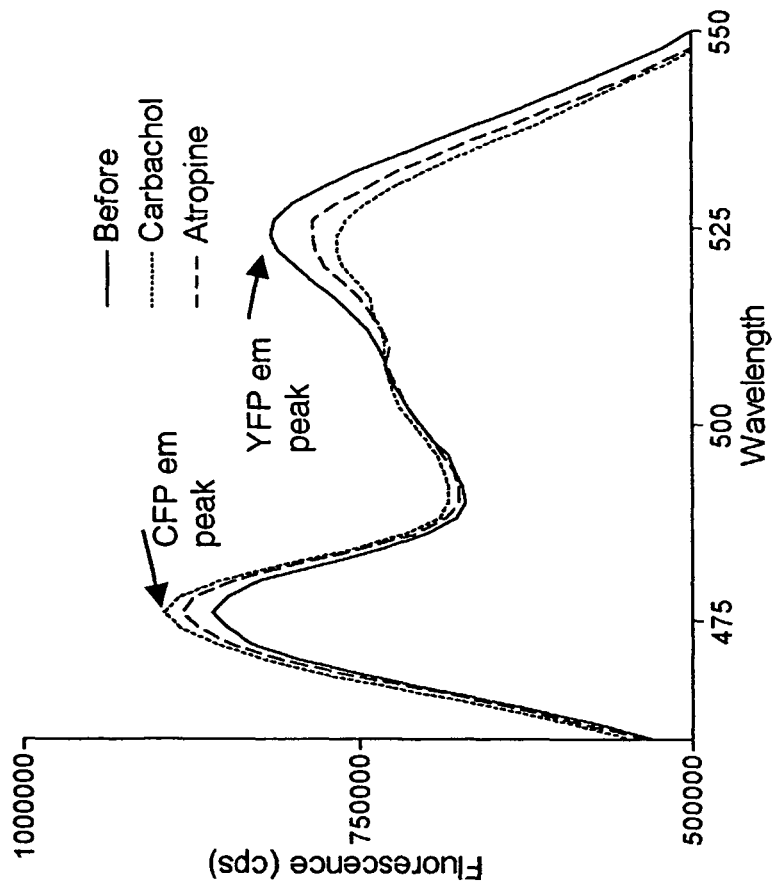

FIG. 22 depicts a graph of fluorescence spectra from biosensor insect cells in response to addition of agonist and antagonist drugs.

Figure 23:
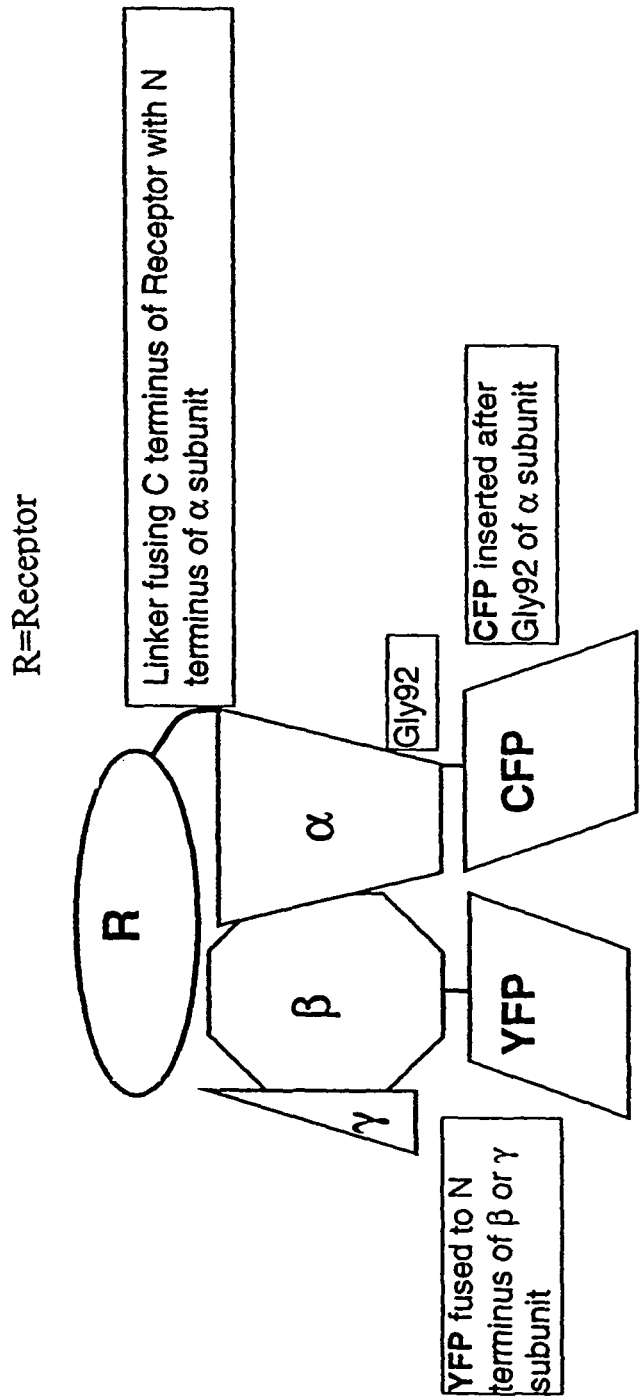

FIG. 23 is a diagrammatic representation of a Receptor-G protein biosensor comprising an α subunit-CFP tethered to the C terminus of a G protein coupled receptor, β subunit and γ subunit-YFP subunit.

Figure 24:
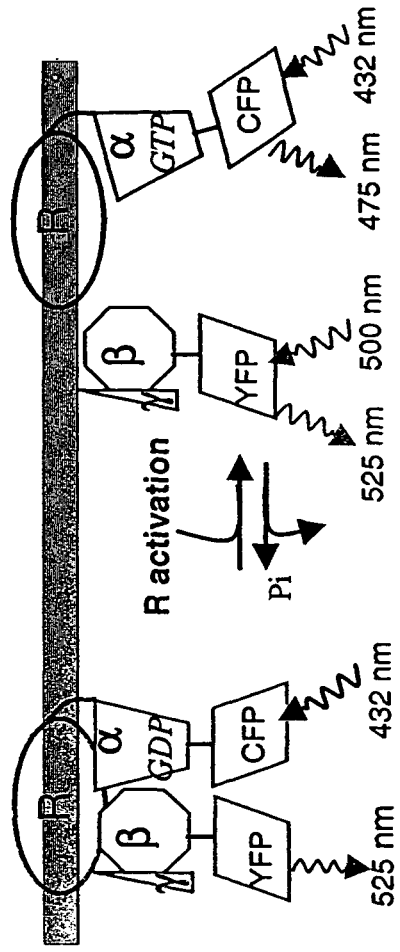

FIG. 24 is a diagrammatic representation of the process of Receptor-G protein biosensor activation and deactivation that results in a corresponding increase and decrease in FRET intensity. Dissociation of subunits may be complete or limited to conformational changes that affect the distance and/or orientation between CFP and YFP. The α subunit will remain in close proximity to the receptor even after activation since it is fused (tethered) to the G protein receptor.

Figure 25:
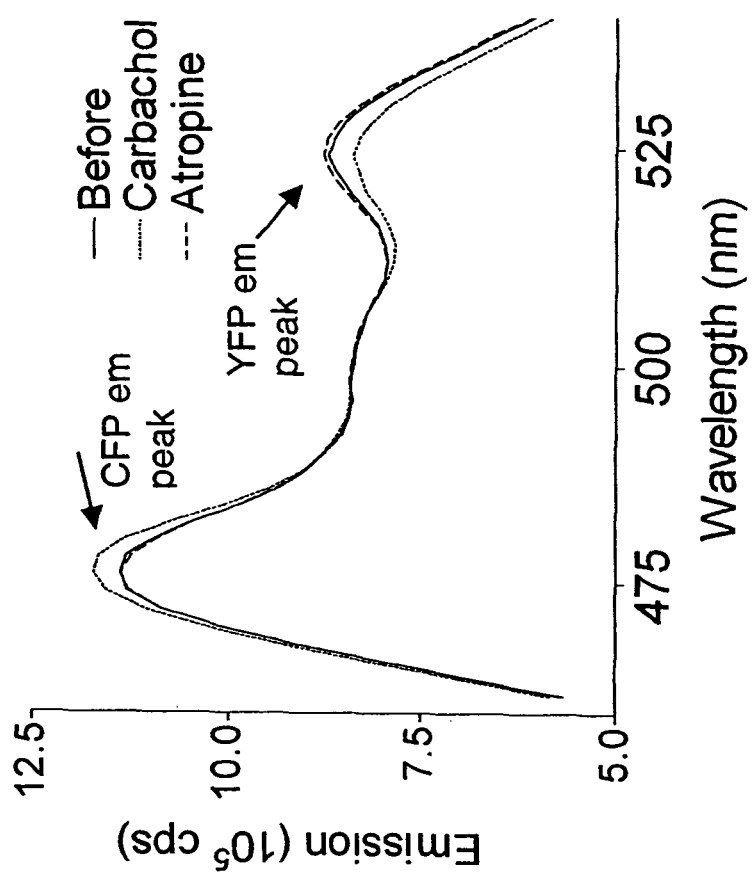

FIG. 25 depicts a graph of fluorescence spectra from insect cells expressing the receptor-G protein biosensor in response to the addition of an agonist drug.

Figure 26:
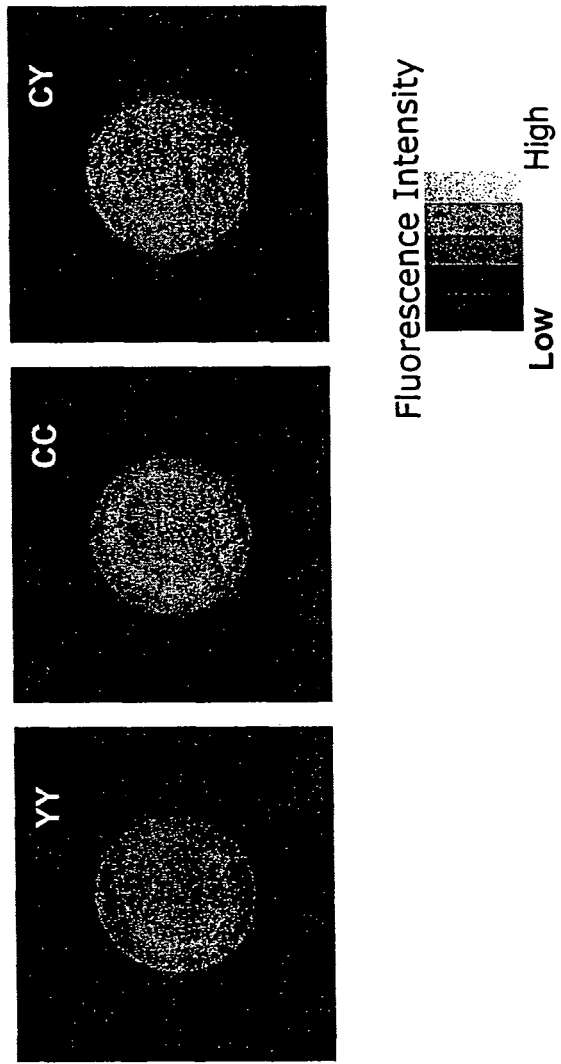

FIG. 26 depicts images of the insect cell(s) as shown in FIG. 25 expressing the Receptor-G protein sensor wherein the CFP tagged alpha subunit is tethered to the receptor and the YFP tagged betagamma complex is also expressed.

Figure 27:
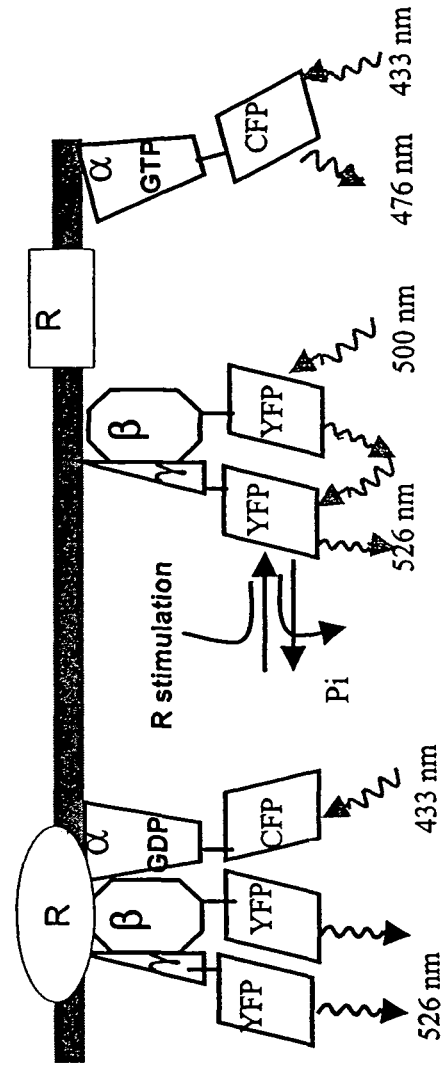

FIG. 27 is a diagrammatic representation of a G protein biosensor comprising an α subunit—CFP with β and γ subunits that are both fused to YFP. The process of receptor activation of this sensor is depicted.

Figure 28:
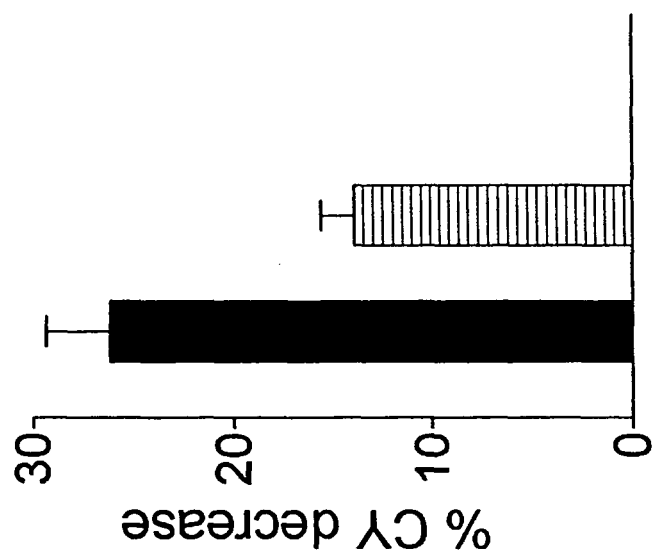

FIG. 28 shows the difference between M2-CHO cells stably expressing α-CFP, β-YFP, γ-YFP (Black) in their emission intensities at 526 nm ith 433 nm excitation before and after addition of carbachol.

Figure 29:
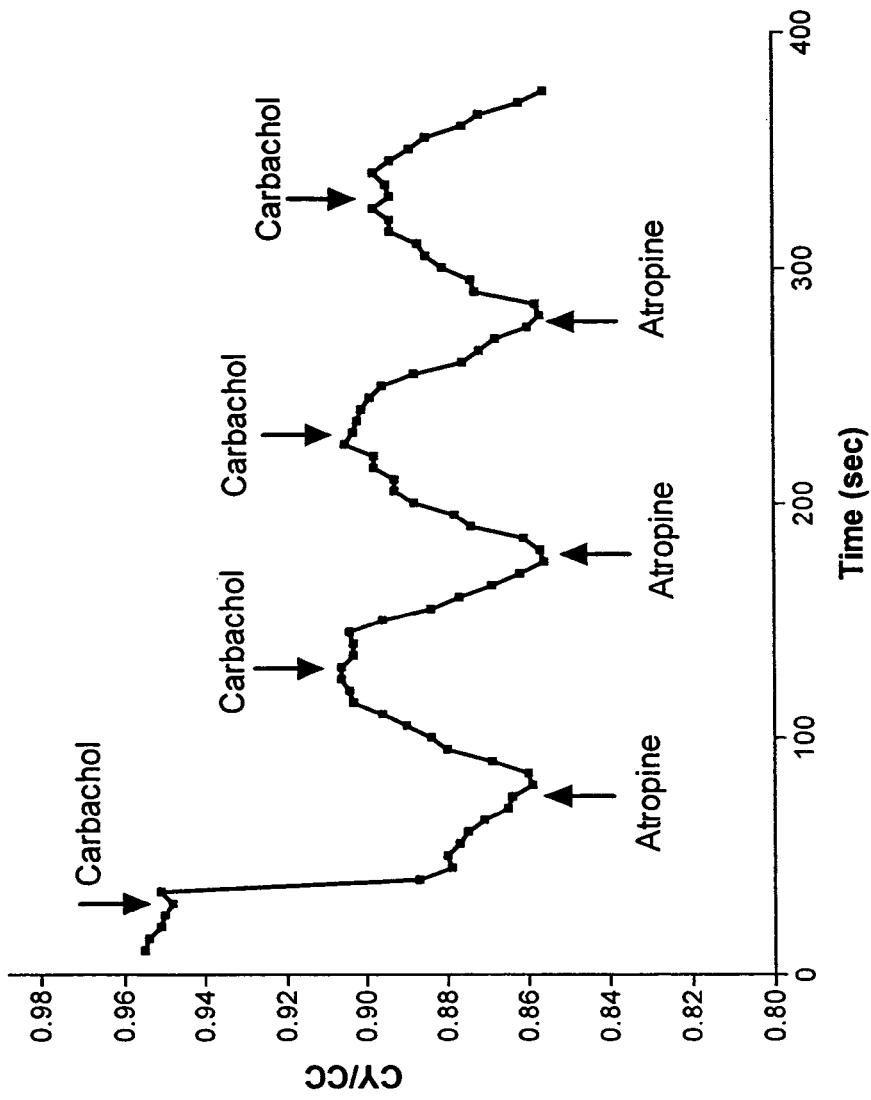

FIG. 29 shows the ability to repetitively measure receptor stimulation with an agonist and inactivation with an antagonist using the same G protein biosensor cell.

Figure 30:
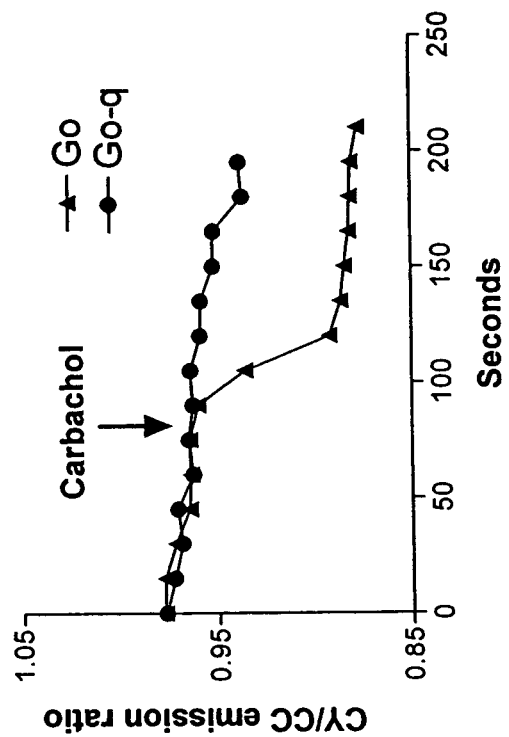

FIG. 30 shows a biosensor containing αo-q-CFP which is a mutant form of αo-CFP with the C terminal domain substituted with the corresponding domain from aq has a strikingly altered property compared to αo-CFP and is no longer activated by the M2 receptor.

Figure 31:
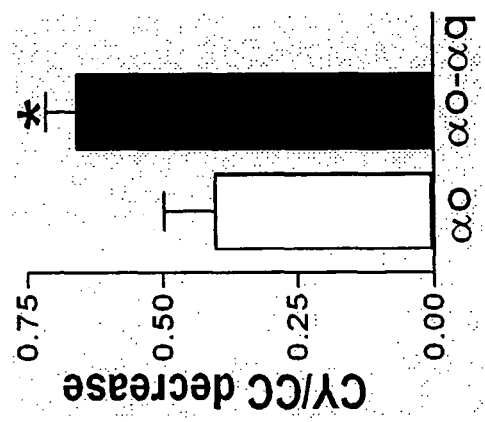

FIG. 31 shows the significantly enhanced ability of a biosensor containing αo-q-CFP to be activated by M3 receptor stimulation compared to the biosensor containing αo-CFP.

DETAILED DESCRIPTION OF THE INVENTION

This invention provides a functional intact biosensor comprising mammalian G protein subunits tagged to mutants of GFP-CFP and YFP that provide a detectable and discernible FRET signal. When expressed in a mammalian cell line and endogenous or introduced/added (expressed) receptors coupled to the G protein biosensors are activated, the FRET signal is significantly decreased. Thus the FRET signal intensity from the biosensor cell provides a direct quantitative, reproducible measure of the activity of a G protein coupled receptor.

In an aspect, a functional G protein biosensor comprises a mammalian α subunit comprising a first amino acid sequence encoding at least one of a first fluorescent and a luminescent protein and a mammalian βγ subunit complex comprising a second amino acid sequence encoding at least one of a second different fluorescent and a luminescent protein, wherein said at least one of a first and at least one of a said second fluorescent and luminescent proteins are at least FRET or BRET capable.

In an aspect, a functional G protein biosensor comprises a mammalian α subunit comprising at least one first amino acid sequence encoding at least one of a first fluorescent protein and luminescent protein fused (tethered) to a mammalian G protein coupled receptor C terminus and a mammalian βγ subunit complex comprising a second amino acid sequence encoding at least one of a second fluorescent protein and a luminescent protein, wherein said at least one first and said at least one second fluorescent protein and luminescent protein are at least FRET or BRET capable. In an aspect, the second fluorescent or luminescent protein are different from first fluorescent or luminescent protein.

In an aspect, the biosensor cell is prepared by expressing the G protein biosensor in a suitable living host cell using a suitable DNA construct.

As used herein, the term "transformation or transfection" includes a process whereby a DNA construct (also called a vector, vector construct or plasmid) carrying foreign (referred to as a heterologous gene) is introduced into and accepted by a suitable host cell. Multiple genes may be operably linked in a single DNA construct and in another aspect multiple genes are introduced using separate vectors. In an aspect, the host cell having the stable DNA construct is cultured to create progeny biosensor cells.

Accordingly in an aspect, a DNA construct (or genetic construct) is provided for the expression of the biosensor in a suitable host cell such as Chinese Hamster ovary cells or progeny thereof comprising an operable linkage of (a) a nucleotide sequence from a suitable cloning vector which capably allows for replication in a mammalian cell such as CHO, (b) regulatory sequences that are capable of allowing transcription and translation of the introduced G protein subunit genes (cDNAs) in CHO cells with or without tagged CFP and YFP, (c) a gene specifying a selectable marker that allows for the selection of cells containing stably integrated vector, and (d) similar construct containing a gene (cDNA) for a mammalian G protein coupled receptor.

In an aspect, the DNA or genetic construct further comprises an expression sequence operably linked to a sequence encoding (and expressing) the expression product.

As used herein, the terms "DNA construct" or "genetic gene construct", "gene" or "cDNA" are used interchangeably herein to, refer to a nucleic acid molecule which may be one or more of the following: regulatory regions, e.g. promoter and enhancer sequences (that are competent to initiate and otherwise regulate the expression of a gene product(s)); any other mutually desired compatible DNA elements for controlling the expression and/or stability of the associated gene product(s) such as polyadenylation sequences; other DNA sequences which function to promote integration of operably linked DNA sequences into the genome of the host cell and any associated DNA elements contained in any nucleic acid system (e.g. plasmid expression vectors) used for the propagation, selection, manipulation and/or transfer of recombinant nucleic acid sequences, sequences encoding proteins that are part of the biosensor or proteins that are functional G protein coupled receptors.

As used herein, the terms "regulatory DNA sequences" or "regulatory regions" or "DNA sequences which regulate the expression of" are used interchangeably herein refer to nucleic acid molecules which function as promoters, enhancers, insulators, silencers and/or other similarly defined sequences which control the spatial and temporal expression of operably linked and/or associated gene products.

In an aspect, the biosensor cell is contained in a suitable housing or compartment which includes a perfusion chamber or suitable liquid composition flow through a containment or housing device whereby a bathing or swabbing composition is provided to the biosensor cell. In an aspect, an inlet composition flows/perfuses through the perfusion chamber and exits, i.e. outflows on an opposite side. In an aspect, the perfusion chamber has separate available openings for composition inflow and composition outflow that dampen or modulate the fluctuations of the liquid level in the working compartment and minimizes bubbles from entering the chamber. In an aspect, a flow connection manifold is provided for such inlet and outlet flow connections to the aforementioned perfusion chamber. If desired, a multiple reducing manifold may be employed at the inlet to the chamber such as a 2:1, 3:1, 4:1, 5:1, 6:1, 7:1 or 8:1 manifold. A temperature controlled perfusion chamber may be employed if desired to control, modulate and regulate temperature of the perfusion chamber.

Typically the inflow composition comprises Hank's buffered saline with 10 mM Hepes ph 7.4 and 1 mg/ml glucose Hank's Balanced Salt Solution ("HBSS") and is prepared external to the perfusion chamber and introduced into the housing or compartment using manual injection or using an automated electronic valve controlled system. HBSS is available from Hyclone, 1725 Hyclone Road, Logan, Utah 84321, U.S.A.

In an aspect, the inflow composition to the perfusion chamber is provided to the perfusion chamber by means of a suitable operable connection thereto such as a manifold.

In an aspect, the inflow composition flow rate is controlled so that the flow rate is about 1-2 ml/min.

In an aspect, the outflow composition is collected from the biosensor cell via outlet manifold or connection and in an aspect, is vacuum aspirated. Flows are controlled by means of suitable valves such as a manual value or an automatic value.

Typically on starting up the biosensor cell and placing it on line i.e. in service, the cell is perfused with HBSS and the cells are brought into the focus of the objective of the microscope. A user selects the image timed exposure and starts to acquire CC and CY images. In an aspect, this is controlled by a software program on a computer such as a personal computer equipped with an operating system and a memory. In an aspect, components of the perfusion chamber including inlet and outlet flow connections, valves, etc. are suitably operably connected and suitably functionally assembled and connected electrically (powered up and the electricity turned on), such as connected to a 110 volt electric supply so that the perfusion chamber and biosensor cell performs in the intended way and function. In an aspect, the valves are manual or are pneumatically or hydraulically operated by an actuator mechanism under human or computer control.

The term "endogenous receptor" refers to an aspect where suitable G protein coupled receptors that are present in a host cell and as such, an exogenous gene capably encoding and expressing a G protein coupled receptor is not necessary in any DNA construct for transcription and translation in CHO cells due to the already present G protein coupled receptors.

The terms "added receptors" and "additional receptors" refers to an aspect where G protein coupled receptors are functionally encoded and expressed in a host cell such as by use of a suitable DNA construct competently integrated into the genome of the host cell, or transiently transfected such that the protein is expressed but the encoding DNA is not integrated in the genome, the construct comprising a nucleic acid encoding and expressing G protein coupled receptors.

As used herein, the term "functional" means that a biosensor cell operates, is fully operational in all its aspects and is a FRET capable or BRET capable biosensor cell.

As used herein the term "G protein" includes guanine nucleotide binding heterotrimeric proteins comprising $\alpha$, $\beta$ and $\gamma$ subunits that are stimulated by G protein coupled receptors resulting in the $\alpha$ subunit binding nucleotide GTP in place of nucleotide GDP.

As used herein the term "FRET" refers to fluorescence resonance energy transfer, a quantum mechanical phenomenon that occurs when two fluorophores or molecules are less than about 80 Å from each other [7]. The two fluorophores involved in FRET have the following properties. The donor fluorophore exhibits an emission spectrum that overlaps the excitation spectrum of the acceptor fluorophore while the individual excitation spectra of the two fluorophores are sufficiently well separated to facilitate independent excitation of each of the fluorophores. Under these conditions when the donor fluorophore is excited, emission of a "FRET signal" can be measured from the acceptor fluorophore. The FRET signal is characteristically visually recognizable by its signal emission from the acceptor fluorophore when the donor alone is excited. The FRET signal is also visually recognizable from the decrease in the fluorescence emission from the donor fluorophore. The FRET signal is also readily recognizable from the increase in the donor fluorophore when the proximity between the donor and acceptor fluorophores is disrupted or when the acceptor fluorophore is bleached.

As used herein the term "FRET signal" refers to the emission of fluorescence from an acceptor fluorophore when the donor fluorophore is excited at the wavelengths that usually result in emission of fluorescence from the donor fluorophore. The term "FRET signal" also refers to the reduction in the fluorescence intensity of the donor fluorophore as a result of FRET from donor to acceptor [7]. (CFP and YFP are illustrative fluorophores.)

In an aspect, the FRET signal from the biosensor is expressed directly as the emission of YFP when CFP is excited or the reduction in CFP emission when FRET occurs or the numerical ratio (quotient) of the YFP emission divided by the CFP emission when CFP is excited or the CFP emission increase when FRET is abrogated.

In an aspect, a functional biosensor produces a discernible, detectable and measurable FRET signal (or BRET signal), an image (of captured fluorescence) of which is competently reliably and accurately captured or acquisitioned by appropriate computer software and is displayed visually on a computer monitor to a person for visual viewing. The intensity and duration of the FRET signal is detectable and is reproducible. One FRET signal may be projected as a trace on a monitor and compared to another FRET signal shown also as a trace on a monitor. A person can then visually compare such FRET signals as they appear on the monitor screen as traces. A determination is then made as to whether one FRET profile is different than or the same as another FRET profile. (Herein the alphabetical letters a, b, c, d, e, etc., are used to denote FRET profiles attained from a biosensor.)

As used herein the term "FRET capable" means that the biosensor is capable of fluorescence resonance energy transfer (FRET) under biosensor conditions enabling such FRET which includes but is not limited to the use of CFP and YFP but extends to the use of other fluorophores attached to the G protein subunits that are capable of FRET. A FRET signal emanating from the biosensor indicates that the biosensor is functional. Detection of a FRET signal is indicative of functional operation of the biosensor.

As used herein, the term "GFP" refers to the Green Fluorescent Protein from *Aequorea victoria* [7].

As used herein, the term "BRET" refers to bioluminescence resonance energy transfer. As used in the specification and claims, the term "FRET" includes and encompasses BRET in all aspects, regards, meanings, and instances of use of the term FRET herein in the specification and claims.

As used herein, the term "CFP" refers to mutant forms of GFP that possess the fluorescence excitation and emission properties similar to the Cyan Fluorescent Protein [7].

As used herein the term "YFP" refers to mutant forms of GFP that possess the fluorescence excitation and emission properties similar to the Yellow Fluorescent Protein including second generation and third generation YFP mutants including Citrine and Venus [7].

In an aspect, useful nonlimiting illustrative fluorescent proteins include modified green fluorescent proteins including but not limited to those disclosed in U.S. Pat. No. 6,319,669 which issued to Roger Tsien on Nov. 20, 2001, Wavelength Engineering Fluorescent Proteins, Modified Green Fluorescent Proteins as disclosed in U.S. Pat. No. 5,625,048 which issued to Roger Tsien on Apr. 29, 1997 and Modified Green Fluorescent Proteins as disclosed in U.S. Pat. No. 5,777,079 which issued to Roger Tsien on Jul. 7, 1998.

As used herein the term "candidate drug molecule" includes at least one of a molecule, ion and chemical moiety for which it is desired to be identified and classified as having potential therapeutic value. The term "molecule" includes a single molecule as well as pools, collections, libraries and assemblies of several different molecules, cells and ions.

As used herein, the term "G protein coupled receptors" include proteins that sense a stimulus signal on one portion of the receptor and communicate it to another portion of the receptor that acts on a heterotrimeric Gprotein(s). Illustratively non-limiting stimulus signals range from but are not limited to one or more of neurotransmitters, hormones, synthetic and natural agonists, light, odorant and gustatory molecules.

Illustrative useful non-limiting mammalian G-protein coupled receptors include Class A Rhodopsin like; Class B Secretin like; Class C Metabotropic glutamate (see "www.g-pcr.org/7tm/").

Characterized or uncharacterized (orphan) receptors include those that are capable of activating G proteins in response to a stimulus, these are also included as G protein coupled receptors.

As used herein, the term "de-orphaning" includes a method of discovering/identifying a molecule as binding to an orphan receptor or likely binding to an orphan receptor and eliciting a predicted FRET profile from the G protein cell biosensor. With the identification of a molecule which binds to an orphan receptor, the orphan receptor is de-orphaned. Genomics and proteomics initiatives of human and other mammals have yielded a vast reservoir of information about the nucleic acid and amino acid sequences of potential G protein coupled receptors without yielding direct information about the stimulus signal including but not limited to natural or synthetic molecules that activate the receptor and the G protein that couples to the receptor. Genomic and proteomic information can indicate that some of these uncharacterized orphan receptors may be at the basis of disease. De-orphaning i.e. identifying the molecules that bind to these receptors, thus is of direct immense therapeutic utility in disease causation studies and diagnosis.

As used herein the term "ligand" includes hormones, neurotransmitters and other natural or synthetic chemical molecules, including ions and chemical moieties that have the capability to specifically and effectively bind to a G protein coupled receptor so as to produce an activated G protein or antagonize such activity initiated by another ligand.

G proteins comprising $\alpha$, $\beta$ and $\gamma$ subunits may be considered as in their respective resting state when bound to GDP. A G protein coupled receptor that is stimulated by a chemical or physical stimulus activates a G protein capable of coupling with it and replaces the GDP with GTP and the G protein is activated. Without being bound by theory, the $\alpha$ subunit is thought to dissociate from the $\beta\gamma$ complex. The hydrolysis of the GTP by the GTPase activity of the $\alpha$ subunit result is thought to deactivate the $\alpha$ subunit and its reassociation with the $\beta\gamma$ complex resulting in a return to the resting state.

As used herein the term "activated G protein heterotrimer" refers to the activation of the G protein $\alpha$ subunit wherein the G protein $\alpha$ of subunit binds GTP giving up GDP and undergoes a conformational change.

Without being bound by theory, it is believed that in the native state a hormone or neurotransmitter molecule binds to a G protein coupled receptor outside the cell and stimulates a change in the G protein coupled receptor that allows the receptor to activate a G protein capable of coupling to the receptor.

The G protein subunits activated in this fashion regulate the activity of various effectors inside the cell that bring about changes in cellular physiology.

As used herein, the term "effector" includes a molecule or chemical moiety which is an intracellular target of G protein $\alpha$ subunit and $\beta\gamma$ complex. Illustratively, nonlimiting major effectors include adenylyl cyclase, phospholipase C and ion channels among others which regulate the levels of second messengers such as cAMP, IP3 as well as ions.

Extracellular signals are sensed by a biosensor cell and transduced into intracellular regulatory changes which result in the final physiological response to the initial stimulus. The intrinsic ability of activated G protein subunits to deactivate is accelerated by a large family of regulatory proteins in mammalian systems. The activated subunits thus go back to the resting state allowing a G protein to act as a molecular switch that is in an "on" or "off" state reflecting the stimulated or unstimulated state of the receptor.

As used herein, the term "agonist" refers to and includes any natural or synthetic molecule, ion or chemical moiety that is capable of stimulating a G protein couple receptor such that a G protein capable of coupling with that receptor is activated.

As used herein, the term "antagonist" refers to and includes any natural or synthetic molecule, ion or chemical moiety that is capable of inhibiting the action of an agonist by interacting directly or indirectly with the receptor.

As used herein, the term "inverse agonist" refers to and includes any natural or synthetic molecule, ion or chemical moiety that is capable of increasing the proportion of inactive receptors in a receptor population comprising active and inactive receptors by binding with higher affinity to the inactive receptors in comparison to its binding with the active receptors [8].

In the G protein biosensor cell herein, association of the G protein $\alpha$ subunit and $\beta\gamma$ complex brings attached fluorophores, respectively CFP and YFP within sufficient geographical proximity for FRET or BRET to occur from excited CFP (donor) to YFP (adaptor). (In an aspect, from a functional biosensor cell comprising a G protein biosensor of the $\alpha$-CFP and $\beta$-YFP$\gamma$ or $\alpha$-CFP and $\beta\gamma$-YFP). The resulting emission from YFP or the reduction in the emission from CFP or the ratio of YFP emission divided by the CFP emission when CFP is excited is the characteristic "FRET signal", the intensity of which is reduced when the G protein biosensor is activated by a receptor when the receptor binds an agonist candidate therapeutic drug molecule.

Illustrative useful living non-limiting competent host mammalian cells include but are not limited to Chinese Hamster ovary cells, Human Embryonic Kidney Cells, COS cells, NIH 3T3 cells, HEK 293 cells, and Swiss 3T3 cells.

Useful non-limiting compounds and molecules which may be added to a biosensor cell for evaluation as a therapeutic candidate include but are not limited to those candidates which are available in libraries of candidate therapeutic drug molecules from industrial, commercial and research laboratory sources. As used herein, the term "molecule" includes a cell.

As used herein "FRET profile" refers to the intensity of the detectable FRET signal measured over a period of time before the addition of candidate therapeutic drug molecules and/or for period of time after the addition of one or more candidate therapeutic drug molecules singly or in succession or collectively. In an aspect, a FRET (or BRET) profile is visually seen as an acquired output of captured or acquisition FRET or BRET from a biosensor or biosensor cell.

This invention has many useful utilities. In an aspect, a method for determining signal transduction activity in a live functional mammalian cell (system) using FRET analysis comprises (reactively) exposing a biosensor cell comprising a mammalian G protein coupled receptor and fluorescent protein tagged mammalian G protein subunits that are at least one of FRET or BRET capable to agonists and antagonists and quantifiably measuring G protein receptor signaling activity non-invasively in the intact cell.

In an aspect, a non-invasive screening method having utility for identifying agonist candidate therapeutic drug molecules comprises using an intact live biosensor cell system FRET signal capable and containing a receptor and a G protein biosensor, which when reactively exposed to a candidate molecule results in reducing the intensity of a FRET signal and indicating that said candidate is an agonist therapeutic drug molecule.

In an aspect, a non-invasive screening method having utility for identifying natural or chemically synthesized candidate agonists and antagonists that bind to uncharacterized or "orphan" mammalian receptors thus de-orphaning orphan receptors comprises using an intact living biosensor cell containing said orphan receptor and fluorescent protein tagged mammalian G protein $\alpha$ and $\beta\gamma$ subunit complexes that are FRET capable and which when reactively exposed to a candidate agonists results in the agonists binding to the receptor eliciting a decrease in an emitted FRET signal and when subsequently the same receptor contacts an antagonist results in an increase of the FRET signal thus identifying respectively candidate agonist(s) and antagonist(s) for the said orphan receptor.

In an aspect, a classification method having utility for natural or chemically synthesized candidate agonists, antagonists and inverse agonist that bind to previously characterized, uncharacterized or "orphan" mammalian receptors, comprises operating an intact living insect cell where a mammalian G protein biosensor comprising a mammalian G protein signaling subunits fused to cyano fluorescent protein and yellow fluorescent protein respectively and capably enabled for at least one of BRET or fluorescence resonance energy transfer (FRET) as well as receptors are expressed using a baculovirus vector and obtaining a FRET profile therefrom in the presence or absence of candidate therapeutic molecules and comparing these obtained FRET profiles to identify agonists, antagonists and inverse agonists for the receptors.

In an aspect, a method for increasing receptor types that will couple to the mammalian functional biosensor comprising mammalian G protein signaling subunit(s) fused to cyan fluorescent protein and yellow fluorescent protein respectively and capably enabled for fluorescence resonance energy transfer by mutationally altering the C terminal tail of the alpha subunit constituent of the biosensor.

In an aspect, a method for altering the intensity of the FRET response from G proteins designed as a mammalian functional biosensor comprising mammalian G protein signaling subunit(s) fused to cyan fluorescent protein and yellow fluorescent protein respectively and capably enabled for fluorescence resonance energy transfer comprises mutationally altering the intrinsic biochemical properties of the subunits that constitute the biosensor.

In an aspect, a method for altering the intensity of the response seen in the FRET profile to agonist, antagonist and inverse agonist molecules comprises mutationally introducing pertussis toxin insensitivity into the mammalian functional biosensor comprising mammalian G protein signaling subunits fused to cyan fluorescent protein and yellow fluorescent protein respectively and capably enabled for fluorescence resonance energy transfer and/or reducing the concentration of endogenous G protein subunits in cells containing the biosensor.

In an aspect, a method for identifying a candidate therapeutic drug molecule is provided which comprises obtaining a FRET profile of a live mammalian functional G protein based cell biosensor comprising a mammalian $\alpha$ subunit comprising at least one of a first amino acid sequence encoding a first fluorescent or luminescent protein and a mammalian $\beta$-YFP$\gamma$ subunit complex comprising a second amino acid sequence encoding a second fluorescent or luminescent protein, wherein said first and said second fluorescent or luminescent proteins are fluorescence resonance energy transfer capable and are expressed in cells containing a previously defined receptor or an orphan receptor (a) in the absence of an added candidate molecule, obtaining a FRET profile of said biosensor over a time period, (b) in the presence of an added molecule comparing said FRET profile (b) with said FRET profile (a) to obtain a comparison of FRET profiles of (b) and (a).

If the comparison shows that FRET signal intensity after the addition of a candidate molecule (b) is less than the FRET signal intensity before the addition of the candidate (a), then one classifies the molecule as an agonist candidate therapeutic drug molecule. If the comparison shows that said FRET profile (b) is similar to said FRET profile (a), then one classifies the molecule as a molecule likely not having agonistic therapeutic value.

As used herein the term "classifies" includes making a determination and assessing the priority of as regards continued and/or future testing and evaluation of a candidate molecule for therapeutic efficacy of a candidate molecule in the development of remedial and preventative and better medicines for humans and other primates. Illustratively, the comparison is visual by visually comparing one FRET signal or one BRET signal with another. If desired, a comparison may be done analytically or computationally as by electronically, such as by comparing two or more FRET outputs ("profile") by the use of suitable comparison software in an operating computer.

In an aspect, a classification includes a determination that a molecule is to advance, remain or be removed from testing, be advanced in testing, keep its placement in testing in research or development. In an aspect, a classification includes a determination that a molecule is not to be further tested, i.e., testing in that molecule is to be terminated. In an aspect, a classification includes a ranking or prioritization of work, such as further work to be done or not to be done on the molecule.

In an aspect, a number of different molecules are added to the biosensor singly or as a pool of various candidates. In an aspect, independent FRET profiles of these candidate molecules are obtained.

In an aspect, a method further comprises adding to the biosensor containing cells, a molecule known as an agonist to provide a FRET profile (c) from the biosensor and subsequently adding to said biosensor a candidate therapeutic drug molecule which provides FRET profile (d) and comparing FRET profile (d) with FRET profile (c). The FRET profile of the known agonist establishes a baseline FRET profile of the biosensor cell for use in other comparisons using the novel methodology and biosensor herein.

If the intensity of the FRET signal from the biosensor after the addition of a candidate molecule in FRET profile (d) is greater than the intensity of the FRET signal from the biosensor after the addition of the known agonist in profile (c), then one classifies the molecule added second as an antagonist therapeutic drug molecule.

If the intensity of the FRET signal after the addition of a candidate molecule in FRET profile (d) does not alter the FRET profile (c), then one classifies the added molecule as not an antagonist.

In an aspect, a method is provided for identifying a therapeutic drug molecule as an inverse agonist which comprises obtaining a FRET profile (e) from biosensor cells containing overexpressed or mutant receptor of defined or orphan status possessing constitutive receptor activity such that the FRET profile (e) of the said biosensor exhibits lower FRET signal intensity from the biosensor than in the profile of the same biosensor in FRET profile (a) from the biosensor.

To classify a candidate molecule as an inverse agonist the cells that exhibit a FRET profile (e) from the biosensor are exposed to candidate molecules and the resulting FRET profile (f) from the biosensor is compared with FRET profile (e) from the biosensor. If the FRET signal intensity has increased after addition of added candidate molecule in FRET profile (f) as compared to the intensity of the signal in FRET profile (e), then the added molecule is classified as an inverse agonist candidate therapeutic drug molecule.

If addition of the candidate does not significantly alter the FRET profile (e), then the added molecule is classified as not likely an inverse agonist.

In an aspect, comparison of the respective FRET profile provides the capability of determining whether the candidate molecule is classified as an agonist, an antagonist or as an inverse agonist.

As an aspect, an in vitro method is provided wherein candidate therapeutic drug molecules to classify the molecules as respectively recited above by obtaining the FRET profiles of partially or fully purified biosensor in the presence of partially or fully purified receptor protein of defined or orphan status and the comparisons of these profiles are made as above illustratively described.

In an aspect, a non-invasive method is provided for classifying therapeutic candidate molecules, where the mammalian G protein biosensor molecules are expressed in insect cells using a baculovirus vector for classifying candidate therapeutic drug molecules by obtaining FRET profiles and comparing them in a manner recited above.

If desired receptor types that will couple to the biosensor are altered by mutationally altering the C terminal tail of the alpha subunit constituent of the biosensor directing the biosensor to couple to and elicit FRET signal changes from receptors that do not normally couple to that biosensor.

In an aspect, a method is provided for eliciting a FRET response from biosensors that are not normally responsive to a receptor by mutationally altering the intrinsic biochemical properties of the subunits that constitute the biosensor such that a FRET signal change is elicited on activation of the mutant biosensor by a receptor.

In an aspect, a method is provided for altering the intensity of the response seen in the FRET profile to agonist, antagonist and inverse agonist molecules by mutationally introducing pertussis toxin insensitivity into the biosensor and/or reducing the concentration of endogenous G protein subunits in cells containing the biosensor cell.

While the term "FRET" has been used in this specification, claims and examples, the terms FRET, FRET capable and the like including BRET are intended to include emission spectra that is capably measured by any appropriate measurement methodology including but not limited to imaging using a fluorescence microscope with suitable optical filters, CCD camera (illustratively a charged coupled device), computer and appropriate computer useful software as well as spectroscopy using a fluorometer [9,10]. In an aspect, a useful imaging system comprises a Zeiss Axioscope/Axiovert or Nikon Eclipse fluorescence microscope, filters from Chroma or Omega, CCD cameras from Hamamatsu or Roper and software from Metamorph from Universal Imaging or IP Lab from Scanalytics and a sufficiently powerful computer capable of running the appropriate software. In an aspect, useful fluorometers include but are not limited to the Spex Fluoromax/Fluorolog from Jobin Yvon Horiba and Cary Eclipse Fluorescence Spectrophotometer from Varian and the Jenway Fluorimeter from Spectronic.

In addition to the above methods, in an aspect, the operation of biosensor cells is observed spectroscopically using a fluorometer. In an aspect, emission spectra including the emission spectra resulting from FRET is measured from biosensor cells using a fluorometer.

As used herein, the term "fluorometer" includes a device or apparatus which measures the duration and intensity of fluorescence. This is generally attached to a fluoroscope. A comparison is made with a standard in providing an output.

In an aspect, the operations of the cells including screening for candidate therapeutic molecules and classifying them as agonists and antagonists can be performed using a fluorometer wherein the biosensor is excited at appropriate wavelengths, the emission spectra are acquired from the cell as a FRET output or FRET profile before and after the addition of candidate therapeutic molecule(s), and the resultant spectra are analyzed in the same manner herein described.

In an aspect, a biosensor comprising a mammalian G protein α subunit tagged with CFP is tethered to the C terminus of a G protein coupled receptor through its N terminus and the β or γ subunit tagged with YFP to provide a detectable and discernible FRET signal. When expressed in a mammalian cell line and the receptor is stimulated with an agonist, the FRET signal is significantly decreased. Thus the FRET signal intensity from the biosensor cell provides a direct quantitative, reproducible measure of the activity of a G protein coupled receptor.

A general procedure follows for designing and operating an online functional biosensor cell providing emission spectra to classify candidate molecules.

Materials: Except listed, all chemicals were from Sigma Aldrich, St. Louis, Mo. Cells were grown in CHO IIIa medium (Life Technologies, 2575 University Ave., St. Paul, Minn. 55113) supplemented with dialyzed fetal bovine serum (Atlanta Biologicals, Atlanta, Ga.), glutamine, penicillin/streptomycin and methoxetrate.

Suitable DNA constructs were designed and made as follows. Sequence GGTACCAAACTAGT (SEQ ID NO: 1) containing Kpn I and Spe I sites was inserted in the site coding for Gly92 and Val93 within the rat αo DNA (carried in a PQE6 vector) using QuikChange (Stratagene, 11011 N. Torrey Pines Road, LaJolla, Calif. 92037). A PCR (polymerase chain reaction) derived CFP fragment with the same sites was introduced and the αo-CFP was transferred into pENTR11 vector (Invitrogen, 1600 Faraday Avenue, P.O. Box 6482, Carlsbad, Calif. 92009). A PCR derived YFP fragment was made with a blunt-ended 5'-terminus and a Kpn I site at the 3'-end with the stop codon removed. A PCR fragment encoding the bovine β1 subunit was made with a Kpn I site at the 5'-end and an EcoR I site at the 3'-end. Both fragments were sequentially inserted into the pENTR11 vector. A bovine γ5 fragment was inserted between EcoRI and XhoI sites of pENTR11. This construct was cut with Xmn I and Sal I, end filled with Klenow polymerase and relegated to remove a Nco I site from the pENTR11 polylinker. Where necessary, the nucleic acid sequence of the DNAs were determined and/or their identity was checked and confirmed by restriction endonuclease digestion.

All were transferred to pDEST12.2 mammalian expression vectors following the manufacturer's instructions (Invitrogen). The number of M2 receptors expressed were about 400,000 receptors per cell. Competent CHO cells expressing M2 were competently transfected with three pDEST12.2 carrying αo-CFP, β1-YFP and γ5. Stable transfectants were selected with G418 and coexpressors were isolated by flow cytometry and confirmed by differential fluorescence microscopy.

In these examples, multiple genes were introduced into a competent host cell (CHO) by means of separate competent DNA constructs in an unlinked co-transformation.

Typically the inflow composition comprises Hank's buffered saline with 10 mM Hepes ph 7.4 and 1 mg/ml glucose (HBSS) and is prepared external to the perfusion chamber and introduced into the chamber using manually by injection or using an automated electronic valve controlled system.

In an aspect, the inflow composition to the perfusion chamber is provided to the perfusion chamber by means of a connection thereto such as a manifold.

In an aspect, the inflow composition flow rate is controlled so that the flow rate is about 1-2 ml/min.

The outflow composition is collected from the biosensor cell via outlet manifold or connection and is vacuum aspirated.

In an aspect, the inflow composition to the perfusion chamber is provided to the perfusion chamber by means of a suitable connection thereto such as a manifold or a single or multi-port inlet and multi-port outlet.

Typically on starting up the biosensor cell it is perfused with the HBSS, the cells are brought into the focus of the objective of the microscope. The user selects the image timed exposure and one starts to acquire CC and CY images. In an aspect, this is controlled by a computer program running and operating suitably on a computer.

Microscopy, image acquisition and FRET analysis (i.e. image capture, recording and analysis) were carried out as follows (generally following the illustration in FIG. 3). Cells were seeded on glass coverslips (25 mm #1 from Warner Instruments) in 35 mm dishes and cultured overnight for imaging. Coverslips containing cells were mounted in a perfusion chamber of 0.36 ml internal volume (RC-21BR from Warner Instrument Corporation, 1141 Dixwell Ave., Hamden, Conn. 06514) containing Hank's Buffered Saline Solution (HBSS) supplemented with 10 mM Hepes pH 7.4 and 1 mg glucose/ml. The perfusion chamber was stage-mounted in an upright Zeiss Axioscope fluorescence microscope. Cells were observed with an Olympus 60× (1.3 NA) or Zeiss 63× (1.4 NA) objective.

Agonists, antagonists or a molecule in the HBSS solution were injected manually (or using an automated valve based system driven pneumatically or by gravity) at a rate of about 2 ml/min for 45 seconds through a secondary inlet of the chamber. Images were acquired at the indicated times. Cells were illuminated with a 50 W mercury lamp (or a 100 W mercury lamp) through a 20% neutral density filter. The filter wheels were run by a Sutter Lambda 10-2 device, a high speed excitation filter wheel that utilizes a direct stepper motor. (Sutter Instrument Company, 51 Digital Drive, Novato, Calif. 94949). In an aspect, power to operate instruments such as the microscope, pumps, motor(s), camera(s), computer(s) control system is supplied by 110 volt electric which is supplied to the instruments and turned on at the startup.

Filters were used in combination with appropriate beam splitters in the filter cube. For CC (cyan) images: D436/20 excitation (x), D480/40 emission (m) and 455DCLP beam splitter; for CY (FRET) images: D436/20x, D535/30m and 455DCLP beam splitter; for YY (yellow) images: the filters D500/20x, D535/30m and 515LP beam splitter. All filters were from Chroma. Images were acquired using a Hamamatsu CCD Orca-ER Camera with 4×4 binning. Exposure times were 1 sec for each CC or CY image. Images were acquired and captured of the FRET signal every 15 sec for a total of 4 or 6 minutes and stored as 12-bit gray scale imagestacks using MetaVue/Metamorph software (Universal Imaging Corporation, 402 Boot Road, Downington, Pa. 19335). Both camera and filter wheels were controlled peripherally using MetaVue from a Dell Computer Workstation (Dell Computer, Houston, Tex.) Images were processed using Metamorph (Universal Imaging) in a Dell Computer Workstation. Images were background subtracted, aligned and plasma membrane regions of entire cells (or most of the cell) were selected after determining that CC (αo-CFP) and YY (β1-YFP) signals were co-localized. Average intensities in these regions were measured. Maximum intensity per pixel in selected regions were ensured to be lower than the maximum value on the available 12-bit gray scale (4095). Ratios of the CY over CC intensities from these regions were plotted to obtain the FRET profiles.

Apart from the FRET signal, the CY emission contains the bleed through of CFP emission and the signal resulting from cross excitation of YFP by the CFP excitation wavelength. In processing the images for determining the spatial localization of the FRET signal, the CY emissions have been directly used as representative of FRET. This approach is valid because first, the agonist and antagonist response are not only detected in the CY emission but also in a corresponding change in the CC emission—a distinguishing property of FRET [9,10]. Second, CY emission changes are highly specific to stimulation or inactivation of muscarinic receptor signaling. Images before treatment with agonist or antagonist were compared with those after treatment using the same gray scale intensities.

Agonist concentration dependence of the decrease in the FRET signal: Images (emission spectra) of live functional biosensor cells were captured and recorded as above for about six minutes. At the 90 sec elapsed time point, cells were stimulated with submaximal concentrations of carbachol (10 nM-10 µM) and at the 210 second time point cells were stimulated maximally (with 1 mM). The regression lines were drawn using GraphPad (Prizm). The percentage of activation by submaximal doses was determined by the formula 100 (Rx−Ro)/(Rm−Ro). Rx, Ro and Rm are the numerical values of the respective regression lines at the 210 second elapsed time point where Ro was the initial baseline, Rx was the submaximal response and Rm was the maximal response.

Figure 1:
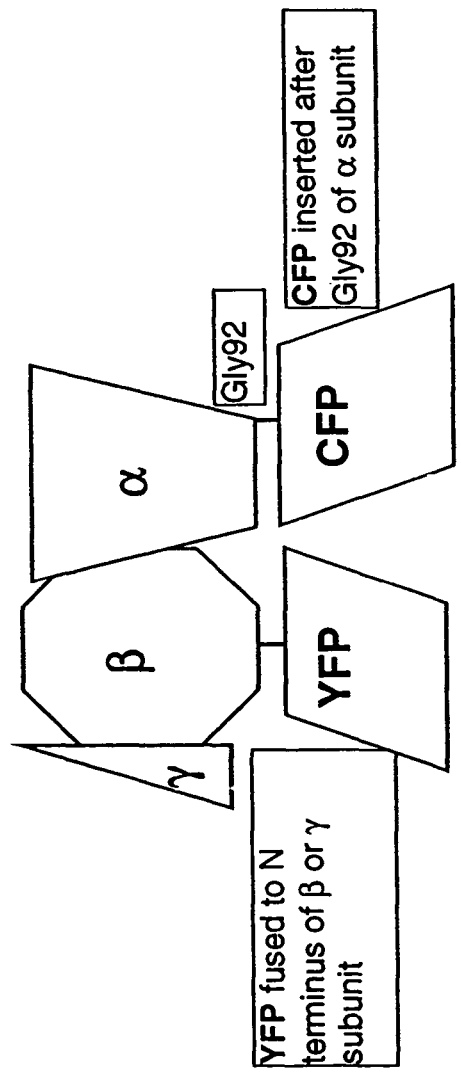
FIG. 1 is a diagrammatic representation of an inventive G protein biosensor comprising fusion proteins α CFP, β YFP and γ subunit based on the crystal structure of Gt.

M2 expressing CHO cells were stably transfected with DNA constructs expressing G protein subunits respectively fused to CFP and YFP. Diagrammatic representations of these fusion proteins based on their crystal structures are shown in FIG. 1. CFP is inserted after Gly92 of the $\alpha$o subunit. YFP is fused to the N terminus of the β1 subunit. The DNA construct was stably integrated into the genome of the M2 expressing CHO cells.

The CFP (molecule) was inserted downstream of Gly92 in $\alpha$o since this region forms a loop that projects away from the βγ complex in the crystal structure of the G protein [11] and the Dictyostelium $\alpha$2 subunit is active when it is fused to CFP in a similar fashion [5]. The YFP molecule is fused to the N terminus of Gβ1 based on our model [12].

Figure 2:
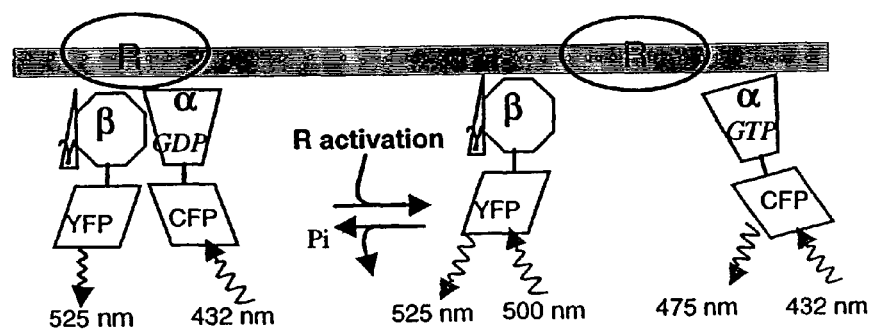
FIG. 2 is a diagrammatic representation of the process of G protein biosensor activation and deactivation that results in a corresponding increase and decrease in FRET intensity. Dissociation of subunits may be complete or limited to conformational changes that affect the distance and/or orientation between CFP and YFP.

Association of the $\alpha$ subunit and the βγ complex potentially brings the YFP and CFP molecules sufficiently close for FRET to occur (FIG. 2). In the heterotrimeric state, excitation of CFP will lead to fluorescence emissions from CFP and also YFP (FRET). If the G protein is activated through receptor activation, excitation of CFP will result in an increase in CFP emission and in the loss of YFP emission containing the FRET signal (FIG. 2). The peak wavelengths of light at which excitation and emission occur for CFP and YFP are noted.

CHO cells stably transfected with the M2 muscarinic receptor were used to stably integrate $\alpha$o-CFP, β1-YFP and γ5 cDNAs into the genome of M2-CHO cells. Biosensor cells expressing all three subunits were imaged as described. Appropriate excitation and emission filters were used to detect and measure emission spectra including CFP emission after CFP excitation (CC), YFP emission with CFP excitation (CY) and YFP emission with YFP excitation (YY).

Figure 3:
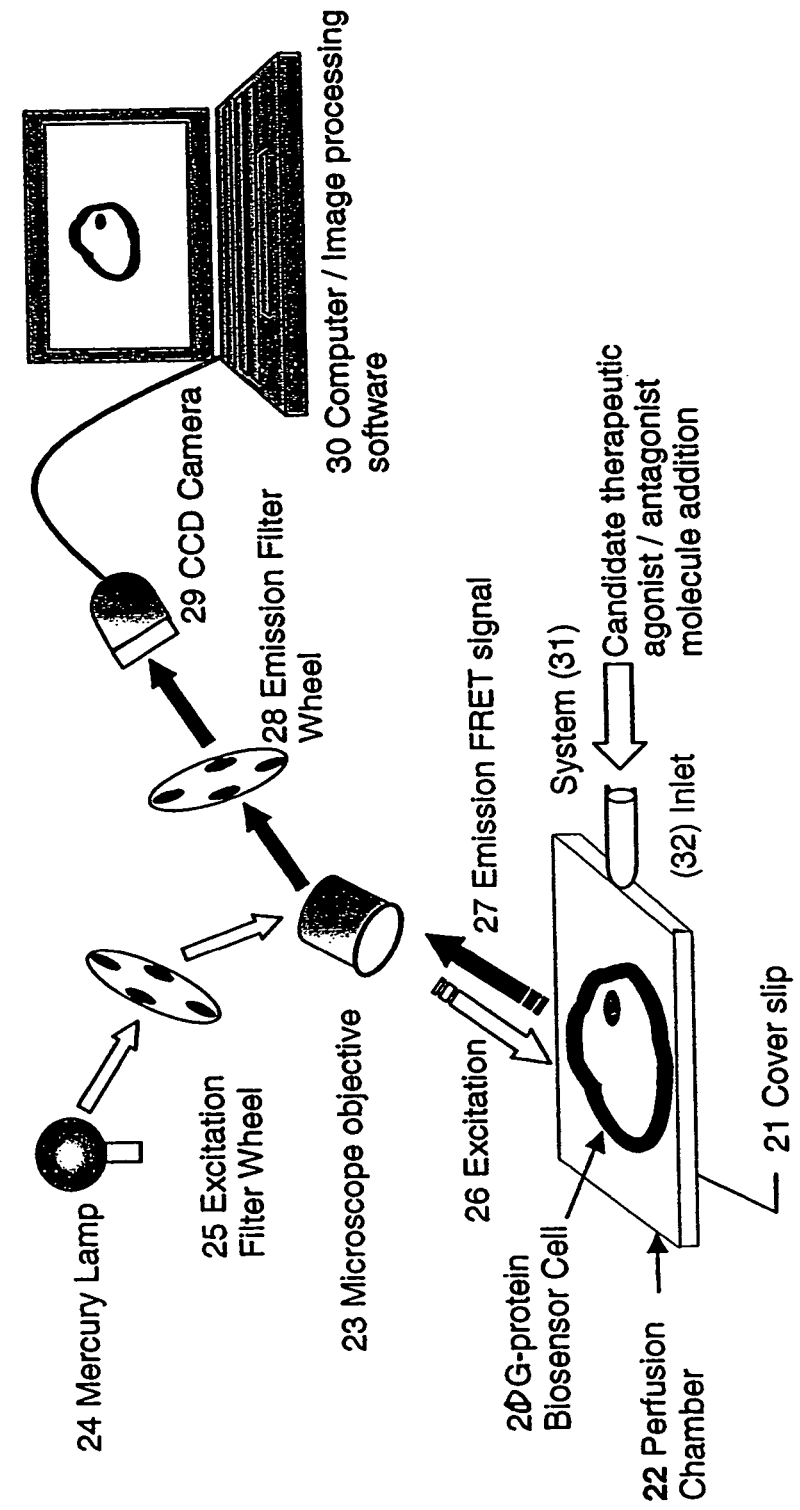
FIG. 3 is a diagram showing flow operation of an illustrative biosensor cell.

FIG. 3 depicts in an aspect, an operational process of acquiring and capturing FRET images for processing from a non-invasive biosensor cell containing a G protein biosensor described in more detail hereinafter in the Detailed Description of the Invention.

As regards FIG. 3, illustratively, G protein biosensor cells (20) are seeded on a glass coverslip and cultured overnight for imaging. Coverslips (21) containing biosensor cells (20) are mounted in perfusion chamber (22) containing appropriate buffer (w/s). Perfusion chamber (22) is stage-mounted in a fluorescence microscope. Cells (20) are observed with a microscope objective (23) with high magnification and numerical aperture. G protein biosensor cell (20) is excited with appropriate wavelengths of light (NS) using mercury lamp (24) and filter (25). The Excitation (26) produces an emitted fluorescence from the functioning G protein biosensor cell (20) as Emission FRET signal (27) which is collected by microscope objective (23) and passed through appropriate emission spectra wheel filter (28) to record an image in a cooled CCD camera (29) (charge coupled device) which transfers the image to a computer (30). The acquired image is processed using appropriate functional imaging software (30). Regions on the cell membrane expressing the biosensor are selected from images collected serially over time and the intensity of the signal emissions of differing spectra under different excitation spectral conditions are determined. Candidate therapeutic agonists, antagonists or molecules are introduced by manual injection or using an automated fluid delivery system containing electronically driven valves into perfusion chamber (22) using inlet (32). In an aspect, the electronically driven valves are powered by 110 volt electric power. (NS=not shown)

It is understood that main and auxiliary components illustrated in FIG. 3 and in the biosensor are communicative with one another in a manner providing for full functionality of the biosensor including all needed electrical supply (including charge coupled devices such as a camera) and liquid conveying means including manifold connections to/from connected tubing, piping etc.

FRET is measured by determining the increase in the CFP excitation after bleaching YFP [10]. However this results in the loss of the YFP signal and is not appropriate for measuring the dynamics of protein-protein interaction. Alternatively, FRET can be measured by determining the numerical CY/CC ratio since FRET results in a decrease in CC emission intensity corresponding to an increase in CY emission intensity [13]. Abrogation of FRET will result in an increase in CC intensity with a corresponding decrease in CY intensity. The numerical ratio thus provides a direct measure of G protein activation over time. The numerical CY/CC ratio is determining by dividing CY by CC and the quotient is the numerical CY/CC ratio.

Cell lines expressing fluorescent subunits showed direct, FRET from $\alpha$-CFP to β-YFPγ complex when the two proteins were co-expressed showing functional operation of the biosensor cell (i.e., it is activated.)

The results of our imaged functional biosensor cells show that $\alpha$-CFP and β-YFPγ complex are localized predominantly in the biosensor cell plasma membrane. The presence of the β-YFP fusion on the cell plasma membrane indicates that it is in complex with the lipid modified γ subunit. The distribution of $\alpha$-CFP is similar to the distribution of the β-YFPγ complex suggesting that the subunits are likely mostly present in the G protein heterotrimer form.

EXAMPLES

Examples (1-9) following are provided to illustrate the invention and are not included for the purpose of limiting the invention in any way.

Example 1

A mammalian G protein biosensor was prepared following the aforedescribed procedure herein functional and produced a FRET signal to test whether FRET occurred from α-CFP to β-YFP. YFP was bleached by illuminating for 4 min using the D500/20× excitation filter (YY set). The intensity of fluorescence emission from CFP was examined before and after bleaching. The CC signal increased about 3 to about 7% after YFP was bleached indicating that the biosensor cell was function and that FRET did occur from CFP to YFP in these fusion proteins This result also showed that the subunit fusions do form a heterotrimer.

The biosensor cell of this biological system is living because it has been cultured on the cover glass to which they are attached during operation and they have multiplied there and also respond to an extracellular signals with expected physiological response. The ability to reproduce and response to the environment characterizes them as living.

The biosensor cell is intact because we have observed the biosensor cells before, during and after operating it and seen the cells under the microscope to retain their cytoplasmic contents within the plasma membrane.

The biosensor cells are functional because they respond to specific stimuli that act on particular receptors evoking anticipated responses.

The biosensor cells are in an appropriate state for starting the capture of signals from the cell when sequential images captured during perfusion with a buffer indicate a stable fluorescence signal in the CC, CY and YY channels.

The stability of the base line signals emitted in the CC, CY and YY channels indicate that the environment of the biosensor cell (perfusion chamber) and the cell are in a functional steady state.

Example 2

The functional G protein biosensor cell responded to an agonist molecule. Images of biosensor cells were acquired (captured) at regular time intervals of 15 sec before and after the addition of a muscarinic acetylcholine receptor agonist drug, carbachol. The FRET profile of the CY/CC ratio was plotted over time and is shown in FIG. 5. The FRET signal intensity decreases in the presence of the agonist drug. FRET images of biosensor cells were acquired and analyzed before and after exposure to carbachol as described in the Procedures for Design and Operation following. Timing of various agonist additions to the biosensor cell are indicated with arrows on FIG. 5. Plots show a downward trend because of partial bleaching over the period of the test. The graph is representative of data from ten tests. The results show that the ratio decreases strikingly when the muscarinic receptor agonist drug, carbachol is introduced into the perfusion chamber containing the cells.

Example 3

The functioning G protein biosensor cell responded quantitatively and reproducibly to an agonist drug. The response of biosensor cells to the addition of varying concentrations of carbachol were measured as described earlier. The FRET signal intensity changes is directly and positively correlated with increases in agonist drug concentration (FIG. 6). Details are provided in Procedures for Design and Operation. Points are means±SEM of three tests. The data curve was fitted using GraphPad (Prizm). FRET signal intensity is decreased by agonist drug addition. Tests were performed as described hereinafter in Detailed Description of the Invention.

The EC50 for carbachol activation of the G protein is about 600 nM which is consistent with the EC50 for carbachol mediated M2 activation of a G protein measured in a reconstituted system (15).

Example 4

The G protein biosensor cell is highly specific in its response. The response of the biosensor cells to the vehicle (buffer alone) and an agonist drug (isoproterenol) specific to a distinctly different receptor, the β adrenergic receptor were measured as described earlier. Both of these treatments had no effect on the FRET signal (FIG. 7). Isoproterenol (100 μM) was added first, followed by the muscarinic receptor specific agonist drug, carbachol (100 μM). Isoproterenol has no effect on FRET signal intensity while carbachol reduced FRET signal intensity.

When cells were pretreated with antagonist drugs specific to muscarinic receptors—atropine—carbachol, the cells no longer elicited the loss of FRET (FIG. 8). FIG. 8 shows a FRET profile (CY/CC) from expressed functional biosensor cells of the effect of addition of carbachol (100 μM), on FRET signal intensity when added in the presence of a muscarinic acetylcholine receptor specific antagonist drug, atropine (10 μM) in functional biosensor cell 1 and functional biosensor cell 2. The data presented is representative of two tests. These test results indicate that the loss of FRET is specific to activation of the muscarinic acetylcholine receptor.

Example 5

The functional G protein biosensor cell responded to an antagonist drug. Based on results from our foregoing Examples 1-4, it is expected that the biosensor made up of G protein subunits will on activation by a receptor emit decreasing FRET signal intensity and when the receptor is inactivated emit increasing FRET signal intensity. Biosensor cells were first exposed to the agonist, carbachol and subsequently to an antagonist, atropine. The FRET profile was obtained from the cells as described earlier. FIG. 9 shows the results of this test. The profile shows that the FRET signal intensity decreases after addition of carbachol. After exposure of the cell to the antagonist atropine however, the FRET signal intensity increases strikingly. (FIG. 9). FRET profile derived from two different biosensor cells are shown. Data presented is representative of five experiments. Images of biosensor cells were acquired and analyzed as described in the Procedures for Design and Operation below hereinafter.

Example 6

G protein biosensor cell activity was measured with FRET profiles of CC and CY emission intensities. The profiles of CC and CY emission intensities corresponding to tests in FIG. 9 are shown in FIG. 10. These profiles show that the CC emission intensity increases after the biosensor cell is exposed to the agonist molecule carbachol. On subsequent addition of the antagonist, atropine, to the biosensor cell, the CC emission intensity decreases. Correspondingly and simultaneously, the CY emission intensity decreases on agonist carbachol addition and increases on the addition of antagonist atropine to the biosensor cells. Agonist and antagonist candidate therapeutic drug molecules can therefore be classified by measuring the response of the G protein biosensor activity using the CC, CY and/or CY/CC ratios. Agonist drug, carbachol induces an increase in CC and a corresponding decrease in CY. Antagonist drug induces a decrease in CC and a corresponding increase in CY. These FRET profiles demonstrate that candidate therapeutic drug molecules can be classified as agonists or antagonists using the CC, CY and/or CY/CC FRET profiles.

The results above demonstrate unambiguously that the CY emission intensity represents changes in the FRET signal seen in response to extracellular signals. To obtain spatial information about the G protein activation and deactivation process in a live cell, the CY images acquired before and after agonist or antagonist perfusion were processed. These images are shown in FIG. 11. Time points are circled in the corresponding CY/CC plot (FIG. 9). Images were processed as described in the Detailed Description of the Invention. After the addition of the agonist, the FRET signal intensity on the membrane decreases significantly. Images acquired after introducing an antagonist shows an increase in the FRET signal intensity in different parts of the cell.

Example 7

Biosensor cells containing the human serotonin receptor instead of the muscarinic receptor responded to the agonist neurotransmitter molecule serotonin. Procedures and materials were substantially the same as those previously recited above under Example 1. Addition of the agonist molecule serotonin to functional biosensor cells decreased the FRET signal intensity significantly as shown in FIG. 12. FIG. 12 is a FRET profile showing the decrease in FRET signal intensity induced by the addition of an agonist neurotransmitter molecule, serotonin (20 µM) to biosensor cells stably expressing human serotonin receptors (Type 1A) instead of muscarinic acetylcholine receptors. One representative result is shown. Results from five tests showed substantially the same responses.

Example 8

Biosensor cells expressing serotonin receptors responded to an antagonist drug specific to the serotonin receptor. Using methods similar to those used above the FRET profile after addition first of an agonist serotonin and subsequently the addition secondly of an antagonist drug, cyanopindolol was obtained (FIG. 13). The agonist induces a decrease in the FRET signal intensity and the antagonist elicits an increase in the FRET signal intensity. One representative result is shown. Three tests performed showed substantially the same responses.

Example 9

Biosensor cell 3 containing the human adenosine receptor instead of the serotonin receptor responded to the agonist drug adenosine N6-Cyclohexyl. Procedures and materials were substantially the same as those previously recited above for Example 1. Addition of the agonist drug adenosine N6-Cyclohexyl to biosensor cells decreased the FRET signal intensity significantly as shown in FIG. 14. One representative result is shown. Three tests performed showed substantially the same responses.

Examples (1-9) demonstrate that the expressed G-protein biosensor effectively operated with different mammalian receptors and mammalian proteins.

Examples (1-9) demonstrate that the G protein biosensor identified specific candidate molecules acting on particular receptors thus establishing a linkage between candidate molecules and associated receptors. This shows that the biosensor cell provides the capability to de-orphan receptors.

FIG. 15 is a FRET profile showing a decrease in FRET signal intensity induced by the addition of carbachol to insect cells (Sf9) expressing the G protein biosensor and the M2 muscarinic acetylcholine receptor. Biosensor and receptor were expressed using the baculovirus system. One representative FRET profile is shown of three tests performed.

FIG. 16 shows FRET profiles from two different biosensor cells containing CFP tagged α subunit and YFP tagged γ subunit and untagged β subunit in CHO cells stably expressing M2 muscarinic receptors. This biosensor demonstrates properties similar to the biosensor α-CFP, β-YFP untagged γ subunit biosensor responding strongly to the addition of carbachol with a decrease in FRET signal intensity.

Preparation of Cells and Fluorometry

CHO cells stably expressing M2 receptor alone or M2 receptor with the biosensor α-CFP/β-YFPγ were plated the day before data acquisition at a density of 1-1.5 million cells in a 100 mm tissue culture dish. The next day the cells were washed with phosphate buffered saline solution, physiological buffer containing 0.02% EDTA was used to suspend cells and finally resuspended in 1-3 ml phosphate buffered saline supplemented with 1 mg glucose/ml after washing with the same buffer. Cells were counted with a hemacytometer and the density of the suspension was adjusted to 2.5 million cells per ml.

All fluorescence spectra were collected with a Fluoromax-3 (JobinYvonHoriba, N.J.) Spectrofluorimeter.

(1) 250 µl of the suspension of CHO cells stably expressing M2 receptor alone were placed in a 500 p.l fluorometric cuvette (Stama, Calif.) within the appropriate cell holder/adaptor. The suspension was maintained under continuous mixing by agitation with a micro magnetic bar. For spectra acquisition, the sample(s) was excited at 422 nm with a band pass of 5 nm and the emission was recorded between 460 and 580 nm with a band pass of 5 nm. The integration time was 2 sec. This spectrum was saved and treated as the 'blank'. Next, spectra was collected as explained above from 250 µl of the suspension of CHO cells stably expressing M2 receptor with the biosensor. The blank spectrum was subtracted from biosensor cell spectrum. In order to ensure that spectra subtraction, and therefore background, was appropriately performed, the intensity at 580 nm was ensured to be the same in both blank cells and biosensor cells. Otherwise, one of the suspensions was diluted with phosphate buffered saline supplemented with 1 mg glucose/ml until the intensity at 580 nm of blank cells and biosensor cells was the same.

FIG. 17 provides an illustrative flow diagram of biosensor cell operation using a spectrofluorometer.

FIG. 18 depicts spectra from cells expressing the biosensor or individual components of the biosensor.

FIG. 19 depicts fluorescence spectroscopy of insect cells in suspension and provides spectra from biosensor cells captured before activation with the agonist, after addition of agonist and then subsequent addition of the antagonist. Spectra was recorded as above before the addition of agonist which was labeled 'initial'. For agonist dependent activation, 1 µl of 25 mM Carbachol was mixed into the suspension. After 60-90 seconds, a new spectra was recorded as explained above which was labeled '+agonist'. Subsequently 2 µl of 10 mM Atropine was mixed into the suspension. After 60-90 seconds, a new spectra was recorded as explained above which was labeled '+antagonist'. The spectrum from blank cells was subtracted from each of these spectra.

FIG. 20 depicts the mean ratios of emission at 526 nm (YFP emission peak) and 480 nm (CFP emission peak) from the different spectra from spectra similar to those in FIG. 19.

FIG. 21 depicts a spectrum from biosensor cells excited at 485 nm to demonstrate presence of YFP in the cells.

FIG. 22 depicts fluorescence spectra from biosensor insect cells in response to addition of agonist and antagonist drugs. The spectra show how insect cells containing the biosensor and particular receptors are used to identify molecules that bind to the receptor and classify them as antagonists/agonists similar to FIG. 19.

Fluorescence Spectroscopy of Mammalian Cells in Suspension.

M2-CHO cells stably expressing various combinations of the tagged G protein subunits were cultured overnight at a density of ~1 million cells in 100 mm tissue culture dishes. Cells for analysis were prepared as above. The cell density was 2.5 million per ml. Spectra of the cells were recorded in 250 µl cuvettes using a Spex Fluoromax-3 spectrofluorometer. Spectra from M2-CHO cells were subtracted from cells expressing G protein sensor or tagged subunits ensuring that emission at 580-600 nm baseline was about the same. For emission spectra resulting from CFP excitation, cell suspensions were excited at 422 nm (5 nm bandpass) and recorded between 460 and 580 nm (5 nm bandpass). For the YFP emission spectra samples were excited at 488 nm (5 nm bandpass) and recorded between 500 and 600 nm. The excitation wavelengths are not the maximums and were picked to facilitate background subtraction. In determining the mean values of the responses to agonist and antagonist the emission intensities at 476-480 nm in the case of CC and the emission intensities at 524-528 nm in the case of CY were averaged and used to determine CY/CC ratios.

Fluorescence Spectroscopy of Insect Cells in Suspension:

Insect cells (Sf9) were infected with baculoviruses expressing M2, α-CFP, β and YFP-γ at a density of $1.0 \times 10^6$ cells/ml. The cells were centrifuged and dissolved in PBS buffer at a density of $3.0 \times 10^6$ cells/ml and measured as 250 µL volume samples in the Spex Fluoromax 3 fluorometer. The excitation wavelength was 433 nm and emission spectrum was recorded from 460-550 nm. The excitation and emission slit-widths were 5 nm, integration time was 0.5 sec/wavelength and monochromator increment was 2 nm. First the spectrum was recorded. Then 2.5 ul of 10 mM carbachol (final concentration of 100 µM) was added and the cells were mixed up and down and the second spectrum was recorded. After that, 2.5 µl of 100 mM atropine (final concentration of 1 mM) was added and a new spectrum was recorded. Untransfected cells were also measured under same conditions and untransfected cell spectrum was subtracted from all three spectra.

The examples above demonstrate that candidate molecules for different receptors can be classified as determined to be agonists or antagonists.

Advantageously, the functional cell based assay satisfies the ever growing demand for a biosensor that identifies and categorizes candidate therapeutic drugs from among candidate drugs collections/libraries in a non-invasive assay. Candidate drugs refers to these drugs/molecules for which an identification and classification or re-classification is desired.

The assay is highly sensitive and will measure relatively low concentrations of candidate molecules conserving expensive compounds.

Advantageously the biosensor cell is useful to provide a screening method for determining therapeutic candidate drugs from among candidate drugs. As used herein the term "candidate therapeutic drug" refers to a drug which has shown activity in a G protein biosensor as an agonist, antagonist or inverse agonist. It is particularly desired to now have the classification system and method for such drugs provided in this invention, including the capability to decide whether to advance a drug to a second level in evaluation such as to advance a drug to secondary screening or advance a drug for testing presently in secondary screening to tertiary screening. The biosensor cell is particularly useful in the increasingly central technology in research and development of better medicines for mankind.

Advantageously use of the biosensor cell provides a non-invasive method which does not disrupt the cell for assaying receptor activity and considerably hastens the process of drug discovery by facilitating the rapid screening of a large library of candidate molecules with a large array of receptor types to classify those molecules which should be further tested or moved further along the research pipeline toward commercialization or in an aspect, those molecules on which further testing should be deferred.

This novel G protein based biosensor cell provides non-invasive rapid screening of candidate drug molecules targeted at G protein coupled receptors in a reproducible and unambiguous fashion. The biosensor cell allows the detection, observation and measurement of signaling properties and dynamics in an on line living intact mammalian cells utilizing mammalian proteins with none, substantially none or minimum disruption to native cellular signaling networks.

Additionally this invention provides receptor stimulated G proteins and a non-invasive non-destructive method (model) of screening candidate molecules using the same in live mammalian cell biosensor cell to identify candidate therapeutic drug molecules from among candidate molecules.

In an aspect, this invention provides a method to identify those candidate molecules which are not therapeutic drug molecules, which in today's world is an ever increasing desired method. It is highly desired to identify the molecules for which research is to continue as well as those for which research is to stop. This invention permits the prioritization of drug candidates based on their performance/evaluation in a biosensor cell.

Also this invention provides receptor stimulated G proteins having subunits respectively fused with a fluorescent or luminescent protein useful in live extraordinarily complex mammalian cells in a biological system having large number of signaling pathways to screen for and to identify therapeutic candidates.

This invention is useful as a tool to identify and/or classify molecules as agonist, antagonist, inverse agonist or innocuous candidate drug molecules of therapeutic value for use in research, industrial and commercial environments and to identify and classify molecules that bind to uncharacterized mammalian orphan G protein coupled receptors.

This invention is also useful as a tool to obtain information about both the temporal and spatial changes in biosensor activity in an intact living cell elicited by candidate therapeutic molecules directed at specific receptors.

This invention is also useful as a tool to identify and/or classify candidate molecules of therapeutic value as agonist, antagonist or inverse agonists of receptors using high content screening.

In an aspect, therapeutic molecules include vaccines, medicines, antidepressants and antibiotics which generally provide a beneficial value to a patient (human or other primate) taking one or more and in need of treatment for a particular medical affliction.

FIG. 25 depicts fluorescence spectra from insect cells expressing CFP tagged α subunit tethered to the M2 receptor and YFP tagged βγ complex in response to addition of an agonist drug when cells were excited at 433 nm, the excitation peak for CFP. The spectra show how insect cells containing this receptor-G protein biosensor can be used to identify molecules that bind to the receptor and classify them as antagonists, agonists and inverse agonists.

Fluorescence spectroscopy of insect cells expressing α-CFP tethered to the M2 receptor and βγ-YFP: Sense primer, AAAGTCGAACATGGGATGTACTCT-GAGCGCAGAGGAGAGAGCCGCC (SEQ ID NO: 2) and anti-sense primer, TTTAGATCTTCAGTACAAGCCA-CAGCCCCGGAGATTGTTGGC (SEQ ID NO: 3), were used to PCR amplify the α-o-CFP DNA. The product was digested with SalI and Bgl II and ligated to the M2 cDNA in the plasmid, pEntr1A, which was cut with the same enzymes downstream of M2. The construct was transferred into the pDest8 vector from Invitrogen using the LR Clonase enzyme. Baculoviruses were generated using standard methods. Insect cells (Sf9) were infected with M2-αo-CFP, β1 and YFP-γ5-wt viruses at a density of $1.0 \times 10^6$ cells/ml. The cells were centrifuged and dissolved in PBS buffer at a density of $2.0 \times 10^6$ cells/ml and measured in 250 μL cells in the Fluoromax 3 fluorometer. The excitations wavelength was set to 433 nm and emission spectrum was recorded from 460-580 nm. The excitation and emission slit-widths were 5 nm, integration time was 0.5 sec/wavelength and monochromator increment was 2 nm. First the spectrum was recorded. Then 2.5 μl of 10 mM carbachol (final conc. is 100 μM) was added and the cells were mixed up and down and the second spectrum was recorded. Untransfected cells were also measured under same conditions and untransfected cell spectrum was subtracted from these spectra.

FIG. 26 shows images of insect cells expressing the Receptor-G protein biosensor from a fluorescence microscope processed using Metavue/metamorph software indicating the presence of the alpha subunit-CFP tethered to M2 on the cell membrane along with betagamma-YFP. Images were acquired for 1.6 sec exposure with a 63× objective and processed without binning. CC channel shows M2-alpha-CFP and the YY channel shows YFP-betagamma cellular distribution.

FIG. 27 is a diagrammatic representation of a G protein biosensor comprising an α subunit-CFP with β and γ subunits that are both fused to YFP. The process of receptor activation of this sensor is depicted.

FIG. 28 shows the difference between M2-CHO cells stably expressing α-CFP, β-YFP, γ (Grey) and α-CFP, β-YFP, γ-YFP (Black) in their emission intensities at 526 nm with 433 nm excitation before and after addition of carbachol. The 526 nm peak intensities were divided by the intensities at 600 nm and presented as percentages (n=2). Cells were examined using fluorescence spectroscopy.

Biosensor cell containing the Go biosensor and expressing the M2 muscarinic acetylcholine receptor responded repeatedly to the addition of an agonist, carbachol and antagonist, atropine, with predictable decreases and increases in FRET signal intensity as shown in FIG. 29. One representative result is shown of four experiments.

FIG. 30 shows that the Go biosensor properties can be altered dramatically by substituting the C terminal domain of αo-CFP in the biosensor with the C terminal domain of αq.

The resultant Go-q sensor was not activated by the M2 muscarinic receptor unlike the Go biosensor. Representative (n=4: αo-q and >50:

FIG. 31 shows that the Go-q biosensor was activated in an enhanced fashion compared to the Go biosensor by the M3 muscarinic receptor, a receptor type that normally couples to Go-q type G proteins. The Go-q biosensor contains αo-q-CFP that is an altered form of αo-CFP in which the C terminal domain of αo was substituted with the C terminal domain of αq. N=5-6 experiments with 20 cells. Asterisk indicate significant difference at $p<0.05$.

Mutant G protein sensors with different C terminal domains can thus be used to specify coupling to different receptor types and can be used tooth identify as well as classify candidate therapeutic molecules that bind to these different types of receptors.

REFERENCES

1. Simon M I, Strathmann M P, Gautam N: Diversity of G proteins in signal transduction. *Science* 1991, 252:802-808.
2. Downes G B, Gautam N: The G protein subunit gene families. *Genomics* 1999, 62:544-552.
3. Neves S R, Ram P T, Iyengar R: G protein pathways. *Science* 2002, 296:1636-1639.
4. Hamm H E: The many faces of G protein signaling. *J Biol Chem* 1998, 273:669-672.
5. Janetopoulos C, Jin T, Devreotes P: Receptor-mediated activation of heterotrimeric G-proteins in living cells. *Science* 2001, 291:2408-2411.
6. Klabunde T, Hessler G: Drug design strategies for targeting G-protein-coupled receptors. *Chembiochem* 2002, 3:928-944.
7. Zhang J, Campbell R E, Ting A Y, Tsien R Y: Creating new fluorescent probes for cell biology. *Nat Rev Mol Cell Biol* 2002, 3:906-918.
8. Teitler M, Herrick-Davis K, Purohit A: Constitutive activity of G-protein coupled receptors: emphasis on serotonin receptors. *Curr Top Med Chem* 2002, 2:529-538.
9. Lippincott-Schwartz J, Snapp E, Kenworthy A: Studying protein dynamics in living cells. *Nat Rev Mol Cell Biol* 2001, 2:444-456.
10. Miyawaki A, Tsien R Y: Monitoring protein conformations and interactions by fluorescence resonance energy transfer between mutants of green fluorescent protein. *Methods Enzymol* 2000, 327:472-500.
11. Lambright D G, Sondek J, Bohm A, Skiba N P, Hamm H E, Sigler P B: The 2.0 A crystal structure of a heterotrimeric G protein. *Nature* 1996, 379:311-319.
12. Azpiazu I, Gautam N: G protein gamma subunit interaction with a receptor regulates receptor-stimulated nucleotide exchange. *J Biol Chem* 2001, 276:41742-41747.
13. Mochizuki N, Yamashita S, Kurokawa K, Ohba Y, Nagai T, Miyawaki A, Matsuda M: Spatio-temporal images of growth-factor-induced activation of Ras and Rap I. *Nature* 2001, 411:1065-1068.

While the invention has been described in terms of various specific embodiments, those skilled in the art will recognize that the invention can be practiced with modification.

What is claimed is:

1. A functional G protein biosensor comprising a mammalian α subunit comprising a first amino acid sequence having at least one of a first fluorescent or luminescent protein, and a mammalian βγ subunit complex, wherein the β subunit comprises a second amino acid sequence having at least one of a second fluorescent or luminescent protein and the γ subunit comprises a third amino acid sequence having at least one of a third fluorescent or luminescent protein, wherein said first, second and third fluorescent or luminescent proteins are at least FRET (Fluorescence Resonance Energy Transfer) or BRET (Bioluminescence Resonance Energy Transfer) capable, wherein the first fluorescent or luminescent protein is different from the second and the third fluorescent or luminescent proteins, and wherein the second fluorescent or luminescent protein is the same as the third fluorescent or luminescent protein.

2. A screening method for screening natural or chemically synthesized candidate agonists and antagonists that bind to previously characterized, uncharacterized or "orphan" mammalian receptors, said method comprising exposing an intact living cell containing said receptors and the G protein biosensor of claim 1 to the candidate agonists and antagonists, wherein the fluorescent protein tagged mammalian G protein α and βγ subunit complex when reactively exposed to the candidate agonists elicits a decrease in FRET signal and when subsequently exposed to an antagonist results in an increase in the FRET or BRET signal; measuring the FRET signal and/or BRET signal to identify candidate agonist(s) and antagonist(s) for said characterized, uncharacterized or orphan receptor.

3. A method for determining signal transduction activity in a live mammalian cell system using FRET analysis, which comprises exposing a biosensor cell comprising a mammalian G protein coupled receptor and the G protein biosensor of claim 1 to agonists and antagonists and quantifiably measuring G protein receptor signaling activity non-invasively in an intact mammalian cell.

4. A non-invasive method for identifying a candidate therapeutic drug molecule, which comprises obtaining a FRET output as a profile over a time period by exposing a live biosensor cell comprising the G protein biosensor of claim 1 to a candidate therapeutic drug molecule, wherein said first, said second and said third fluorescent or luminescent proteins are expressed in cells containing a receptor or an orphan receptor (a) in the absence of the added candidate therapeutic drug molecule; (b) in the presence of the added candidate therapeutic drug molecule; and comparing said FRET profile (b) with said FRET profile (a) to obtain a comparison of the FRET profile of (b) with the FRET profile of (a).

5. A method in accordance with claim 4 wherein if said comparison shows emitted FRET signal intensity after the addition of the candidate therapeutic drug molecule (b) is less than the FRET signal intensity before the addition of the candidate therapeutic drug molecule (a), then one classifies the candidate therapeutic drug molecule as an agonist candidate therapeutic drug molecule, and if the comparison shows that said FRET profile (b) is similar to said FRET profile (a), then one classifies the candidate therapeutic drug molecule as a molecule likely not having agonistic therapeutic value.

6. A method in accordance with claim 5 wherein a number of different candidate therapeutic drug molecules are added to said biosensor containing cells, singly or as a pool of various candidate therapeutic drug molecules and FRET profiles of these candidate therapeutic drug molecules are obtained to classify candidate therapeutic drug molecules.

7. A non-invasive screening method for identifying agonist candidate therapeutic drug molecules comprising exposing an intact live biosensor cell system containing a receptor and the G protein biosensor of claim 1 to a candidate therapeutic drug molecule and measuring the reduction of the intensity of said FRET signal which indicates that said candidate therapeutic drug molecule is an agonist therapeutic drug molecule.

8. A non-invasive screening method for identifying antagonistic activity of a candidate therapeutic drug molecule comprising exposing an intact live biosensor cell system containing a receptor and the G protein biosensor of claim 1 to a known agonist and subsequently to a candidate therapeutic drug molecule, said agonist being capable of binding to the receptor, measuring the reduction of an emitted FRET signal, measuring the increase in the intensity of the FRET signal after subsequent binding of the candidate therapeutic drug molecule, and comparing the intensity of the FRET signal subsequent to the addition of the said agonist alone to the FRET signal after binding of the candidate therapeutic drug molecule, which indicates that the candidate therapeutic drug molecule is a therapeutic antagonist molecule.

9. A non-invasive screening method for identifying natural or chemically synthesized candidate agonists and antagonists that bind to uncharacterized or "orphan" mammalian receptors thus de-orphaning orphan receptors, said method comprising exposing an intact living biosensor cell containing the orphan receptor and the G protein biosensor of claim 1 to the candidate agonists and antagonists, measuring a decrease in an emitted FRET signal when the fluorescent protein tagged mammalian G protein α subunit and βγ complex subunit are reactively exposed to the candidate agonists when agonists bind to the receptor, measuring an increase of the FRET signal when the same receptor subsequently contacts an antagonist, and identifying candidate agonist(s) and antagonist(s) for the said orphan receptor.

10. A method in accordance with claim 9 wherein said method further comprises adding to the biosensor containing cells, a molecule known as an agonist to provide a FRET profile (c) and subsequently adding to biosensor a candidate therapeutic drug molecule which provides FRET profile (d) and comparing the FRET profile (d) with the FRET profile (c).

11. A method in accordance with claim 10 wherein if the FRET signal after the addition of a candidate therapeutic drug molecule in FRET profile (d) is greater than the intensity of the FRET signal after the addition of the known agonist in profile (c), then one classifies the molecule added second as an antagonist candidate therapeutic drug molecule.

12. A method in accordance with claim 10 wherein if the FRET signal after the addition of a candidate therapeutic drug molecule in FRET profile (d) does not alter the FRET profile (c), then one classifies the added candidate therapeutic drug molecule is not an antagonist.

13. A method in accordance with claim 10 wherein one or a number of different molecules are added to the biosensor containing cells, singly or as a pool of various candidate therapeutic drug molecules and FRET profiles of these candidate molecules are obtained to classify candidate therapeutic molecules.

14. A classification method for natural or chemically synthesized candidate agonists, antagonists and inverse agonist that bind to previously characterized, uncharacterized or "orphan" mammalian receptors, said method comprising exposing an intact living insect cell wherein the G protein biosensor of claim 1 as well as receptors are expressed using a baculovirus vector to candidate therapeutic drug molecules, obtaining a FRET profile therefrom in the presence or absence of the candidate therapeutic drug molecules and comparing these obtained FRET profiles to identify agonists, antagonists and inverse agonists for the receptors.

15. The functional G protein biosensor of claim 1, wherein the first, second and third fluorescent or luminescent proteins are FRET capable and the addition of an agonist for the G protein coupled receptor reduces the FRET signal intensity from the biosensor.

16. A method of classifying candidate therapeutic molecules as agonists, antagonists or inverse agonist comprising exposing receptor-G protein biosensor cells comprising the G protein biosensor of claim 1 to candidate therapeutic molecules, wherein the receptor-G protein biosensor cells express the fluorescent protein tagged α subunit tethered to a G protein coupled receptor and the fluorescent protein tagged βγ complex and screening for predicted changes in the FRET profile from these cells in response to the addition of the candidate therapeutic molecules by quantifiably measuring G protein receptor signaling activity non-invasively in an intact mammalian cell.

17. A live functional G protein biosensor cell comprising the G protein biosensor of claim 1.

18. A method for identifying and classifying multiple candidate therapeutic molecules comprising exposing the same G protein biosensor cell comprising the G protein biosensor of claim 1 to agonistic and antagonistic compounds by repetitive treatment, wherein the fluorescent protein tagged mammalian G protein α and βγ subunit complex when reactively exposed to the agonistic compound elicits a decrease in FRET signal and when subsequently exposed to the antagonist compound results in an increase in the FRET or BRET signal; measuring the FRET and/or BRET signal; and analyzing FRET and/or BRET signal, thereby identifying and classifying the multiple candidate therapeutic molecules.

19. A method for identifying and classifying a single candidate therapeutic molecule by exposing the same G protein biosensor cell comprising the G protein biosensor of claim 1 to agonistic and antagonistic compounds by repetitive treatment, wherein the fluorescent protein tagged mammalian G protein α and βγ subunit complex when reactively exposed to the agonistic compound elicits a decrease in FRET signal and when subsequently exposed to the antagonist compound results in an increase in the FRET or BRET signal measuring the FRET and/or BRET signal; and analyzing FRET and/or BRET signal, thereby identifying and classifying the candidate therapeutic molecule.

* * * * *